(12) United States Patent
Gerngross

(10) Patent No.: US 7,981,660 B2
(45) Date of Patent: *Jul. 19, 2011

(54) METHODS FOR PRODUCING MODIFIED GLYCOPROTEINS

(75) Inventor: Tillman U. Gerngross, Hanover, NH (US)

(73) Assignee: Glycofi, Inc., Lebanon, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/549,062

(22) Filed: Aug. 27, 2009

(65) Prior Publication Data

US 2010/0021991 A1    Jan. 28, 2010

Related U.S. Application Data

(62) Division of application No. 11/271,235, filed on Nov. 10, 2005, now Pat. No. 7,629,163, which is a division of application No. 09/892,591, filed on Jun. 27, 2001, now Pat. No. 7,029,872.

(60) Provisional application No. 60/214,358, filed on Jun. 28, 2000, provisional application No. 60/215,638, filed on Jun. 30, 2000, provisional application No. 60/279,997, filed on Mar. 30, 2001.

(51) Int. Cl.
  *C12N 1/15* (2006.01)
  *C07K 14/00* (2006.01)

(52) U.S. Cl. ...................................... 435/254.1; 530/395

(58) Field of Classification Search .......................... None
See application file for complete search history.

(56) References Cited

U.S. PATENT DOCUMENTS

| | | |
|---|---|---|
| 4,414,329 A | 11/1983 | Wegner |
| 4,617,274 A | 10/1986 | Wegner |
| 4,683,293 A | 7/1987 | Craig |
| 4,775,622 A | 10/1988 | Hitzeman et al. |
| 4,808,537 A | 2/1989 | Stroman et al. |
| 4,812,405 A | 3/1989 | Lair et al. |
| 4,818,700 A | 4/1989 | Cregg et al. |
| 4,837,148 A | 6/1989 | Cregg |
| 4,855,231 A | 8/1989 | Stroman et al. |
| 4,857,467 A | 8/1989 | Sreekrishna et al. |
| 4,879,231 A | 11/1989 | Stroman et al. |
| 4,882,279 A | 11/1989 | Cregg |
| 4,885,242 A | 12/1989 | Cregg |
| 4,925,796 A | 5/1990 | Bergh et al. |
| 4,929,555 A | 5/1990 | Cregg et al. |
| 4,935,349 A | 6/1990 | McKnight et al. |
| 5,002,876 A | 3/1991 | Sreekrishna et al. |
| 5,004,688 A | 4/1991 | Craig et al. |
| 5,032,516 A | 7/1991 | Cregg |
| 5,032,519 A | 7/1991 | Paulson et al. |
| 5,047,335 A | 9/1991 | Paulson et al. |
| 5,122,465 A | 6/1992 | Cregg et al. |
| 5,135,854 A | 8/1992 | MacKay et al. |
| 5,166,329 A | 11/1992 | Cregg |
| 5,272,066 A | 12/1993 | Bergh et al. |
| 5,324,663 A | 6/1994 | Lowe |
| 5,595,900 A | 1/1997 | Lowe |
| 5,602,003 A | 2/1997 | Pierce et al. |
| 5,683,899 A | 11/1997 | Stuart |
| 5,707,828 A | 1/1998 | Sreekrishna et al. |
| 5,766,910 A | 6/1998 | Fukuda et al. |
| 5,834,251 A | 11/1998 | Maras et al. |
| 5,844,093 A | 12/1998 | Kettleborough et al. |
| 5,849,904 A | 12/1998 | Gerardy-Schahn et al. |
| 5,854,018 A | 12/1998 | Hitzemane et al. |
| 5,861,293 A | 1/1999 | Kojiri et al. |
| 5,910,570 A | 6/1999 | Elhammer et al. |
| 5,945,314 A | 8/1999 | Prieto et al. |
| 5,945,322 A | 8/1999 | Gotschlich |
| 5,955,347 A | 9/1999 | Lowe |
| 5,955,422 A | 9/1999 | Lin |
| 5,962,294 A | 10/1999 | Paulson et al. |
| 6,017,743 A | 1/2000 | Tsuji et al. |
| 6,069,235 A | 5/2000 | Davis et al. |
| 6,096,512 A | 8/2000 | Elhammer et al. |
| 6,204,431 B1 | 3/2001 | Prieto et al. |
| 6,300,113 B1 | 10/2001 | Landry |
| 6,410,246 B1 | 6/2002 | Zhu et al. |
| 6,602,684 B1 | 8/2003 | Umana et al. |
| 6,946,292 B2 | 9/2005 | Kanda et al. |

(Continued)

FOREIGN PATENT DOCUMENTS

| | | |
|---|---|---|
| EP | 0 905 232 | 3/1999 |
| EP | 1 054 062 | 11/2000 |

(Continued)

OTHER PUBLICATIONS

Chiba et al., "Production of Human Compatible High Mannose-type (Man5GlcAc2) Sugar Chains in *Saccharomyces cerevisiae*", The Journal of Biological Chemistry 273(41): 26298-26304 (Oct. 1998).*

(Continued)

*Primary Examiner* — Anand U Desai

(57) ABSTRACT

Cell lines having genetically modified glycosylation pathways that allow them to carry out a sequence of enzymatic reactions, which mimic the processing of glycoproteins in humans, have been developed. Recombinant proteins expressed in these engineered hosts yield glycoproteins more similar, if not substantially identical, to their human counterparts. The lower eukaryotes, which ordinarily produce high-mannose containing N-glycans, including unicellular and multicellular fungi are modified to produce N-glycans such as $Man_5GlcNAc_2$ or other structures along human glycosylation pathways. This is achieved using a combination of engineering and/or selection of strains which: do not express certain enzymes which create the undesirable complex structures characteristic of the fungal glycoproteins, which express exogenous enzymes selected either to have optimal activity under the conditions present in the fungi where activity is desired, or which are targeted to an organelle where optimal activity is achieved, and combinations thereof wherein the genetically engineered eukaryote expresses multiple exogenous enzymes required to produce "human-like" glycoproteins.

21 Claims, 2 Drawing Sheets

U.S. PATENT DOCUMENTS

| | | | |
|---|---|---|---|
| 7,029,872 | B2 | 4/2006 | Gerngross |
| 7,064,191 | B2 | 6/2006 | Shinkawa et al. |
| 7,214,775 | B2 | 5/2007 | Hanai et al. |
| 7,259,007 | B2 | 8/2007 | Bobrowicz |
| 7,326,681 | B2 | 2/2008 | Gerngross |
| 7,332,299 | B2 | 2/2008 | Hamilton |
| 7,365,163 | B2 | 4/2008 | Hanna |
| 7,449,308 | B2 | 11/2008 | Gerngross |
| 7,465,577 | B2 | 12/2008 | Bobrowicz |
| 7,514,253 | B2 | 4/2009 | Nett |
| 7,517,670 | B2 | 4/2009 | Umana |
| 7,598,055 | B2 * | 10/2009 | Bobrowicz et al. .......... 435/69.1 |
| 7,625,756 | B2 | 12/2009 | Hamilton |
| 7,629,163 | B2 | 12/2009 | Gerngross |
| 2003/0157108 | A1 | 8/2003 | Presta |
| 2003/0175884 | A1 | 9/2003 | Umana et al. |
| 2004/0191256 | A1 | 9/2004 | Raju |
| 2005/0170452 | A1 | 8/2005 | Wildt et al. |
| 2005/0260729 | A1 | 11/2005 | Hamilton |
| 2005/0265988 | A1 | 12/2005 | Choi et al. |
| 2006/0024292 | A1 | 2/2006 | Gerngross et al. |
| 2006/0024304 | A1 | 2/2006 | Gerngross et al. |
| 2006/0029604 | A1 | 2/2006 | Gergross et al. |
| 2006/0034828 | A1 | 2/2006 | Gerngross et al. |
| 2006/0034829 | A1 | 2/2006 | Gerngross et al. |
| 2006/0034830 | A1 | 2/2006 | Gerngross et al. |
| 2006/0040353 | A1 | 2/2006 | Davidson et al. |
| 2006/0177898 | A1 | 8/2006 | Gerngross |
| 2006/0257399 | A1 | 11/2006 | Gerngross et al. |
| 2006/0286637 | A1 | 12/2006 | Hamilton |
| 2007/0037248 | A1 | 2/2007 | Bobrowicz et al. |
| 2007/0105127 | A1 | 5/2007 | Gerngross |
| 2007/0154591 | A1 | 7/2007 | Andersen |
| 2008/0274162 | A1 | 11/2008 | Nessa et al. |

FOREIGN PATENT DOCUMENTS

| | | |
|---|---|---|
| EP | 1176195 | 1/2002 |
| EP | 1 211 310 | 6/2002 |
| EP | 1 239 047 | 9/2002 |
| EP | 1297172 | 4/2003 |
| EP | 1522590 | 4/2005 |
| JP | 8-336387 | 12/1996 |
| JP | 11-103158 | 4/1999 |
| WO | WO 96/21038 | 7/1996 |
| WO | WO 98/05768 | 2/1998 |
| WO | WO 99/31224 | 6/1999 |
| WO | WO 99/40208 | 8/1999 |
| WO | WO 99/54342 | 10/1999 |
| WO | WO 00/61739 | 10/2000 |
| WO | WO 01/14522 | 3/2001 |
| WO | WO 01/25406 | 4/2001 |
| WO | WO 01/36432 | 5/2001 |
| WO | WO 01/60860 | 8/2001 |
| WO | WO 02/00856 | 1/2002 |
| WO | WO 02/00879 | 1/2002 |
| WO | WO 02/97060 | 12/2002 |
| WO | WO 03/011878 | 2/2003 |
| WO | WO 03/025148 | 3/2003 |
| WO | WO 03/031464 | 4/2003 |
| WO | WO 03/056914 | 7/2003 |
| WO | WO 2004/003194 | 1/2004 |
| WO | WO 2004/074458 | 9/2004 |
| WO | WO 2004/074461 | 9/2004 |
| WO | WO 2004/074497 | 9/2004 |
| WO | WO 2004/074498 | 9/2004 |
| WO | WO 2004/074499 | 9/2004 |
| WO | WO 2004/104165 | 12/2004 |
| WO | WO 2005/065019 | 7/2005 |
| WO | WO 2005/090552 | 9/2005 |
| WO | WO 2005/100584 | 10/2005 |
| WO | WO 2005/106010 | 11/2005 |
| WO | WO 2006/014679 | 2/2006 |
| WO | WO 2006/014683 | 2/2006 |
| WO | WO 2006/014685 | 2/2006 |
| WO | WO 2006/014725 | 2/2006 |
| WO | WO 2006/071280 | 7/2006 |
| WO | WO 2006/071856 | 7/2006 |
| WO | WO 2006/014726 | 9/2006 |
| WO | WO 2007/028144 | 3/2007 |
| WO | WO 2007/029054 | 3/2007 |

OTHER PUBLICATIONS

Abeijon et al., "Molecular Cloning of the Golgi apparatus uridine diphosphate-N-acetylglucosamine transporter from *Kluyveromyces lactis*," Proc. Natl. Acad. Sci. USA 93:5963-5968 (1996).

Adachi et al., "Mus Musculus Adult Male Testis cDNA, Riken full length enriched library, clone: 4931438M07 product: mannosidase 2, alpha 2, full insert sequence" XP002293645, Database accession No. AK029913 Abstract, Database EMBL, Dec. 21, 2002.

Alani et al., "A Method for Gene Disruption that Allows Repeated Use of URA3 Selection in the Construction of Multiply Disrupted Yeast Strains," Genetics 116, 541-545, Aug. 1987.

Abdel-Salam et al., "Expression of mouse anticreatine kinase (MAK33) monoclonal antibody in the yeast Hansenula Polymorpha", App. Microbiol. Biotechnol. 56:157-164 (2001).

Allison, Daniel S., et al., "Mutations in the Signal Sequence of Prepro-α-Factor Inhibit Both Translocation into the Endoplasmic Reticulum and Processing by Signal Peptide in Yeast Cells," Molecular and Cellular Biology, vol. 9(11):4977-4985 (1989).

Altman et al., "Processing of Asparagine-linked Oligosaccharides in Insect Cells: Evidence for Alpha-Mannosidase II," *Glycoconj. J* 12(2):150-155 (1995).

Altman et al., "Insect cells as hosts for the expression of recombinant glycoproteins," *Glycoconj. J.* 16(2):109-123 (1999).

Al-Rawi et al., (2004) Synthesis and biochemical properties of reversible inhibitors of UDP-N-acetylglucosamine 2-epimerase. Angew. Chem. Int. Ed. Engl. vol. 43, No. 33, pp. 4366-4370.

Altschul et al., "Basic Local Alignment Search Tool", J. Mol. Biol. 215:403-410 (1990).

Altschul et al., "Gapped BLAST and PSI-BLAST: a new generation of protein database search program", Nucleic Acids Res. 25:3389-3402 (1997).

Andersen et al., "The Effect of Cell-Culture Conditions on the Oligosaccharide Structures of Secreted Glycoproteins," *Curr Opin Biotechnol*, 5(5):546-549, Oct. 1994.

Aoki et al., "Expression and activity of chimeric molecules between human UDP-galactose transporter and CMP-sialic acid transporter," *J. Biochem.* (Tokyo), 126(5):940-50, Nov. 1999.

Bardor et al., "Analysis of the N-glycosylation of recombinant glycoproteins produced in transgenic plants," *Trends in Plant Science* 4(9): 376-380 (1999).

Bause and Burbach, "Purification and Enzymatic Properties of Endo-α1,2-Mannosidase from Pig Liver Involved in Oligosaccharide Processing," *Biol. Chem.* 377:639-646 (1996).

Beaudet et al., "High-level expression of mouse Mdr3 P-glycoprotein in yeast *Pichia pastoris* and characterization of ATPase activity," *Methods Enzymol* 292: 397-413 (1998).

Berka et al., "The Filamentous *Fungus aspergillus-niger* var *awamori* as Host for the Expression and Secretion of Fungal and Non-Fungal Heterologous Proteins," *Abstr Papers Amer Chem Soc* 203: 121-BIOT (1992).

Berninsone et al., "The Golgi Guanosine Diphosphatase is Required for Transport of GDP-Mannose Into the Lumen of *Saccharomyces cerevisiae* Golgi Vesicles," *J. Biol. Chem.*, 269(1):207-211, Jan. 1994.

Berninsone et al., "Regulation of yeast Golgi glycosylation. Guanosine diphosphatase functions as a homodimer in the membrane," *J. Biol. Chem* 270(24): 14564-14567 (1995).

Berninsone et al., "Functional Expression of the Murine Golgi CMP-Sialic Acid Transporter in *Saccharomyces cerevisiae*," *J. Biol. Chem.* 272(19):12616-12619, May 1997.

Bianchi et al., "Transformation of the yeast *Kluyveromyces lactis* by new vectors derived from the 1.6 μm circular plasmid pKD1," *Current Genetics*, 12:185-192, 1987.

Bobrowicz, Piotr et al., Engineering of an artificial glycosylation pathway blocked in core oligosaccharide assembly in the yeast *Pichia pastoris*: production of complex humanized glycoproteins with terminal galactose: Glycobiology, vol. 14(9): 757-766 (2004).

Boehm et al., "Disruption of the KEX1 Gene in *Pichia Pastoris* Allows Expression of Full Length Murine and Human Endostatin," *Yeast*, 15:563-572 (1999).

Boeke et al., "A positive selection for mutants lacking orotidine-5'-phosphate decarboxylase activity in yeast: 5-fluoro-orotic acid resistance", Mol. Gen. Genet. 197:345-346 (1984).

Bonneaud et al., "A family of low and high copy replicative, integrative and single-stranded *S. cerevisiae/E. coli* shuttle vectors," *Yeast* 7(6): 609-615 (1991).

Borreback et al., "Human Momoclonal antibodies produced by primary in vitro immunization of peripheral blood lymphocytes", Proc. Natl. Acad. Sci. USa, 85:3995-3999 (1988).

Boutin, "Myristoylation," Cell. Signal. 9(1):15-35 (1997).

Bretthauer et al., "Glycosylation of *Pichia pastoris*-derived proteins," *Biotechnol Appl Biochem* 30(Pt 3): 193-200 (1999).

Bretthauer et al., "Genetic engineering of *Pichia pastoris* to humanize N-glycosylation of proteins," *TRENDS in Biochem*, 21(11): 459-462 (2003).

Brockhausen et al., "Control of glycoprotein synthesis. The use of oligosaccharide substrates and HPLC to study the sequential pathway for N-acetylglucosaminyltransferases I, II, III, IV, V and VI in the biosynthesis of highly branched N-glycans by hen oviduct membranes," Biochem. Cell Biol. 66:1134-1151 (1988).

Bucket et al., "Cloning and nucleotide sequence of heavy and light chain cDNAs from a creatine-kinase-specific monoclonal antibody", Gene, 51:13-19 (1987).

Cadwell and Joyce, Randomization of Genes by PCR Mutagenesis:, PCR Methods Applic. 2:28-33 (1992).

Callewaert et al., "Use of HDEL-tagged Trichoderma reesei mannosyl oligosaccharide 1,2-α- D-mannosidase for N-glycan engineering in *Pichia pastoris*", FEBS Lett. 503(2-3):173-178 (2001).

Cabanes-Macheteau et al., "N-Glycosylation of a mouse IgG expressed in transgenic tobacco plants," Glycobiology, vol. 9, No. 4. pp. 365-372 (1999).

Callewaert et al., "Use of HDEL-Tagged *Trichoderma reesei* Mannosyl Oligosaccharide 1,2∀D-Mannosidase for *N*-glycan Engineering in *Pichia pastoris*," FEBS Letters, 503(2-3):173-8, 2001.

Carninci et al., XP-002293371, AK030141, dated Dec. 5, 2002, "Mus musculus adult male testis cDNA . . . ".

Cereghino et al., "Heterologous protein expression in the methylotropic yeast *Pichia pastoris*," *FEMS Microbiology Reviews*, 24(1): 45-66 (2000).

Cereghino et al., "New selectable marker/auxotrophic host strain combinations for molecular genetic manipulation of *Pichia pastoris*" Gene, 263:159-169 (2001).

Chandrasekaran et al., "Purification and Properties of Alpha-D-Mannose:beta-1,2-N-acetylglucosaminyl-transferases and alpha-D-Mannosidases from Human Adenocarcinoma," *Cancer Res.*, 44(9):4059-68, Sep. 1984.

Chapman et al., "Effects of glucose starvation and puromycin treatment on lipid-linked oligosaccharide precursors..", Arch. Biochem. Biophys. 260(1):320-333 (1988).

Chen et al., (1995) Effect of retinoic acid on the structure of N-glycans on the surface of human hepatocarcinoma cells and its enzymatic mechanism, J. Cancer Res. Clin. Oncol. vol. 121, No. 7, pp. 397-401.

Chiba et al., "Production of Human Compatible High Mannose-type (Man$_5$GlcNAc$_2$) Sugar Chains in *Saccharomyces cerevisiae*," *J. Biol. Chem.*, 273(41):26298-26304, Oct. 1998.

Choi et al., "Use of combinatorial genetic libraries to humanize N-linked glycosylation in the yeast *Pichia pastoris*," *Proc. Natl. Acad. Sci.* USA 100(9):5022-502 (2003).

Chui et al., "Genetic Remodeling of Protein Glycosylation in vivo Induces Autoimmune Disease," *Proc. Natl. Acad. Sci.*, USA 98:1142-1147 (2001).

Chui et al., "Alpha-mannosidase-II Deficiency Results in Dyserythropoieis and Unveils and Alternate Pathway in Oligosaccharide Biosynthesis," *Cell*, Jul. 11, 1997; 90(1):157-67.

Cole, et al., "Modeling the growth, survival and death of microorganisms in foods: the UK food micromodel approach," J. Cell Biochem 23(3-4) 265-275 (1994).

D'Agostaro et al., "Molecular cloning and expression of cDNA encoding the rate UDP-N-acetylglusamine:alpha-6-D-mannoside beta-1,2-N-acetylglucosaminyltransferase II", J. Biol. Chem, vol. 270, No. 25, pp. 15211-15221 (1995).

Daniel et al, "Mammalian Alpha-Mannosidases—Multiple Forms but a Common Purpose?", *Glycobiology*, 4, 551-566, Oct. 1994.

Davies et al., "Expression of GnTIII in a Recombinant Anti-CD20 CHO Production Cell Line:; Expression of Antibodies with Altered Glycoforms Leads to an Increase in ADCC Through Higher Affinity for FcyRIII", Biotechnol. Bioeng., 74(4):288-294 (2001).

Dempski and Imperiali, "Oligosaccharyl transferase: gatekeeper to the secretory pathway," *Curr. Opin. in Chem. Biol*. 6:844-850 (2002).

Dennis et al., "Protein glycosylation in development and disease", Bioessays, 21(5):412-21 (1999).

Dente, "Human alpha-1-acid glycoprotein genes," Prog. Clin. Biol. Res 300:85-98 (1989).

Duman et al., "O-mannosylation of *Pichia pastoris* cellular and recombinant proteins", Biotechnology Appl. Biochem., vol. 28, pp. 39-45 (1998).

Duvet et al., "Cytosolic Deglycosylation Process of Newly Synthesized Glycoproteins Generates Oligomannosides Possessing One GLcNAc Residue at the Reducing End," *Biochem J.*, 335, 1998, 389-396.

Eades et al., "Characterization of the Class I alpha-Mannosidase Gene Family in the Filamentous Fungus *Aspergillus nidulans*," *Gene*, Sep. 5, 2000; 225(1):25-34.

Eckhardt et al., "Molecular Cloning of the Hamster CMP-Sialic Acid Transporter," *Eur. J. Biochem.*, 248(1):187-192 (1997).

Foster et al., "Cloning and Sequence Analysis of GmII, a Drosophila Melanogaster Homologue of the cDNA Encoding Murine Golgi alpha-Mannosidase II," *Gene* 154 (1995) 183-186.

Fujita et al., Biochem. & Biophys. Res. Comm., vol. 238 (1997), pp. 779-783, "Five crucial carboxyl residues of 1,2-alpha-mannosidase . . . ".

Fukuta et al., "Remodeling of sugar chain structures of human interferon-γ", Glycobiology, vol. 10, pp. 421-430 (2000).

Gavel et al., "Sequence differences between glycosylated and non-glycosylated Asn-X-Thr/Ser acceptor sites: implications for protein engineering," Protein Eng., 3:433-43 (1990).

Gerngross, Tillman U., "Advances in the production of human therapeutic proteins in yeasts and filamentous fungi", Nature biotechnology, vol. 22(11):1409-1414 (2004).

Gleeson, Paul A. "Targeting of Proteins to the Golgi Apparatus," *Histochem. Cell Biol.*, 109:517-532 (1998).

Gleeson et al (1983) Control of glycoprotein synthesis. J. Biol. Chem. vol. 258, No. 10, pp. 1662-1673.

Gonzalez, Daniel S et al: "The Alpha-Mannosidases: Phylogeny and Adaptive Diversification" Molecular Biology and Evolution, vol. 17, No. 2, Feb. 2000, pp. 292-300, XP002293609 ISSN: 0737-4038.

Goochee et al., "The Olgosaccharides of Glycoproteins: Bioprocess Factors Affecting Oligosaccharide Structure and Their Effect on Glycoprotein Properties", Biotechnology, 9(12):1347-1355 (1999).

Graham et al., "Compartmental Organization of Golgi-specific Protein Modification and Vacuolar Protein Sorting Events Defined in Yeast *sec* 18 (*NSF*) Mutant," *J. Cell. Biol.*, 114(2): 207-218 (1991).

Grard et al., "Oligomannosides or Oligosaccharide-lipids as Potential Substrates for Rat Liver Cytosolic ∀-D-Mannosidase," *Biochem. J.*, 316: 787-792 (1996).

Grasziano et al., "Construction and Characterization of a Humanized Anti-γ-Ig Receptor Type I (FcγRI) Monoclonal Antibody", J. Immunol., 155(10):4996-5002 (1995).

Guillen et al., "Mammalian Golgi apparatus UDP-*N*-acetylglucosamine transporter: Molecular Cloning by Phenotypic Correction of a Yeast Mutant," *Proc. Natl. Acad. Sci. USA*, 95(14):7888-7892 (1998).

Hamilton et al., "Production of Complex Human Glycoproteins in Yeast," *Science* 301:1244-1246 (2003).

Hamilton, Stephen R. et al., "Humanization of Yeast to Produce Complex Terminally Sialylated Glycoproteins", Science, vol. 313:1441-1443 (2006).

Hard, et al, "Isolation and structure determination of the intact sialylated N-linked carbohydrate chains of recombinant human follitropin expressed in Chinese hamster ovary cells," Eur. J. biochem., vol. 193, No. 1, pp. 263-271 (1990).

Harkki et al., "A Novel Fungal Express System—Secretion of Active Calf Chymosin from the Filamentous Fungus *Trichoderma-reesei*," *Bio-Tech* 7:596-603 (1989).

Harris B.R..: "*Caenorhabditis elegans* Cosmid F58H1" XP002293610, Protein F58H1.1, Abstract, Databaase EMBL Jul. 13, 1996.

Haworth, Robert S., et al., "Intracellular pH in *Schizosaccharomyces pombe*-Comparison with *Saccharomyces cerevisiae*", Molecular and Cellular Biochemistry, vol. 124, pp. 131-140 (1993).

Hayes et al., "Carbohydrate Compositions of the Rabbit Plasminogen Isozymes", J. Arch. Biochem. Biophys., 171:651-655 1975).

Hernandez et al., "Structure of the Phosphorylated N-linked Oligosaccharides from the mnn9 and mnn 10 Mutants of *Saccharomyces cerevisiae*", The Journal of Biological Chemistry, 264(23):13648-13659 (1989).

Herscovics, Processing glycosidases of *Saccharomyces cerevisiae, Biochim. Biophys. Acta* 1426:275-285 (1999).

Hiraizumi et al., "Characterization of Endomannosidase Inhibitors and Evaluation of Their Effect on *N*-Linked Olligosaccharide Processing during Glycoprotein Biosynthesis," *J. Biol. Chem.* 268(13):9927-9935 (1993).

Hiraizumi et al., "Ligand Affinity Chromatographic Purification of Rat Liver Golgi Endomannosidase," *J. Biol. Chem.* 269(7)4697-4700 (1994).

Huffaker et al., "Yeast mutants deficient in protein glycosylation", Proc. Natl. Acad. Sci. USA, 80(24):7466-70 (1983).

Ichishima et al., "Molecular and Enzymic Properties of Recombinant 1,2-∀-Mannosidase from *Aspergillus saitoi* Overexpressed in *Aspergillus oryzae* Cells," 1999; *Biochem. J.*, 339(Pt 3): 589-597.

Inamori et al., Molecular Cloning and Characterization of Human GnT-IX, a Novel β1,6-N-Acetylglucosaminyltransferase that is specifically expressed in the Brain, J. Biol. Chem., vol. 278, No. 44, pp. 43102-43109 (2003).

Ishida et al., "Molecular Cloning and Characterization of a Novel Isoform of the Human UDP-Galactose Transporter, and of Related Complementary DNAs Belonging to the Nucleotide-Sugar Transporter Gene Family", J. Biochem., (Tokyo) 120(6):1074-1078 (1996).

Ishida et al., "Molecular Cloning and Functional Expression of the Human Golgi UDP-*N*-Acetylglucosamine Transporter," *J. Biochem.*, 126(1):68-77 (1999).

Jarvis et al., "Isolation and Characterization of a Class II alpha-mannosidase cDNA from Lepidopteran Insect Cells," *Glycobiology*, 1997; 7(1):113-127 (1997).

Jarvis et al., "Engineering N-glycosylation pathways in the baculovirus-insect cell system," *Curr Opin Biotechnol* 9(5): 528-33 (1998).

Jefferis, "Glycosylation of Human IgG Antibodies", Biopharma, 14:19-26 (2001).

Juranic et al., Antiproliferative action of water extracts of seeds or pulp of five different raspberry cultivars, Food Chem., vol. 93, pp. 39-45 (2005).

Kainuma et al., "Coexpression of α1,2 galactosyltransferase and UDP-galactose transporter efficiently galatosylates *N*- and *O*-glycan in *Saccharomyces cerevisiae,*" *Glycobiology*, 9(2):133-141 (1999).

Kaletta et al., "The peptide HDEF as a new retention signal is necessary and sufficient to direct proteins to the endoplasmic reticulum", FEBS Lett., vol. 434, No. 3, pp. 377-381 (1998).

Kalsner et al., "Insertion into *Aspergillus nidulans* of functional UDP-GLcNAc: α3-D-mannoside β-1,2-*N*-acetylglucosaminyl-transferase I, the enzyme catalysing the first committed step from oligomannose to hybrid and complex N-glycans," *Glycoconj. J.*, 12(3):360-370 (1995).

Kawar et al., "Insect Cells Encode a Class II ∀-Mannosidase with Unique Properties," *J. Biol. Chem.*, 276(19):16335-16340 (2001).

Khatra et al., "Some kinetic properties of human milk galactosyltransferase," *Eur. J. Biochem.* 44:537-560 (1974).

Kim, Jae Hong et al., "Nonivasive measurement of the pH of the endoplasmic reticulum at rest and during calcium release", Proc. Natl. Acad. Sci. USA, vol. 95, pp. 2997-3002 (1998).

Kojima, N. et al., "Characterization of Mouse ST8Sia II (STX) as a neural cell adhesion molecule-specific polysialic acid synthase", The Journal of Biological Chemistry, vol. 271, No. 32, pp. 19457-19463 (1996).

Krezdorn et al., "Human β1,4 galactosyltransferase and α2,6 sialytransferase expressed in *Saccharomyces cerevisiae* are retained as active enzymes in the endoplasmic reticulum," *Eur. J. Biochem.*, 220(3): 809-17 (1994).

Kyte and Doolittle, "A Simple Method for Displaying the Hydropathic Character of a Protein," *J. Mol. Biol.* 157:105-132 (1982).

Lal et al., "Isolation and Expression of Murine and Rabbit cDNAs Encoding an α1,2- Mannosidase Involved in the Processing of Asparagine-Linked Oligosaccharides," *J. Biol. Chem.*, 1994. 269(13): 9872-9881.

Lal et al. "Substrate Specificities of Recombnant Murine Golgi α1,2-Mannosidase IA and IB and Comparison with Endoplasmic Reticulum and Golgi Processing α1,2-Mannosidases," *Glycobiology* 8(10):981-995, 1998.

Lee et al., "Sequential §-integration for the regulated insertion of cloned genes . . . ", Biotechnol. Prog., vol. 13, pp. 368-373 (1997).

Lehle and Tanner, "Membrane-Bound Mannosyl Transferase in Yeast Glycoprotein Biosynthesis," *Biochem. Biophys. Acta*, 350(1): 225-235, 1974.

Leung et al., "A method for random mutagenesis of a defined DNA segment using a modified polymerase chain reacation", Techniqure, 1:11-15 (1989).

Li et al., "Optimization of humanized IgGs in glycoengineered *Pichia pastoris*" Nature Biotech., vol. 24, pp. 210-215 (2006).

Lifely et al., "Glycosylation and biological activity of CAMPATH-1H expressed in different cell lines . . . ", Glycobiology, vol. 5, pp. 813-822 (1995).

Llopis, J., et al., "Measurement of cytosolic, mitochondrial, and Golgi pH in single living cells with green fluorescent proteins", Proc. Natl. Acad. Sci. USA, vol. 95, pp. 6803-6803 (1998).

Lopez, et al., "Microheterogeneity of the oligosaccharides carried by the recombinant bovine lactoferrin expressed in mamestra brassicae cells," Glycobiology., vol. 7, No. 5, pp. 635-651 (1997).

Lowder et al., "Monoclonal antibodies—therapeutic and diagnostics uses in malignancy", Western J. Med., vol. 193, pp. 810-816 (1985).

Lu et al., "Cloning and Disruption of the b-Isopropylmalate Dehydrogenase Gene of *Pichia stipitis* with URA3 and Recovery of the Double Auxotroph," *Appl. Microbiol. Biotechnol.*, 49 (2): 141-146 (1998).

Lubas and Spiro, "Evaluation of the Role of Rat Liver Golgi Endo-α-D-mannosidase in Processing *N*-linked Oligosaccharides," *J. Biol. Chem.* 263(8):3990-3998 (1988).

Lussier et al., "The *KTR* and *MNN1* mannosyltransferase families of *Saccharomyces cerevisiae,*" *Biochimica et Biophysica Acta* 1426: 323-334 (1999).

Madden et al., "Applications of Network BLAST Server", Meth. Enzymol., 266:131-141 (1996).

Makoto, T., et al., "Trial for Molecular Breeding of Yeast for the production of glycoprotein therapeutics", Trends in Glycoscience and Glycotechnology, vol. 9 (suppl.):S29-S35 (1997).

Malissard et al., "Expression of functional soluble forms of human beta-1, 4-galactosyltransferase I, alpha-2-6-sialytransferase, and alpha-1, 3-fucosyltransferase VI in the methylotrophic yeast *Pichia pastoris*," Biochem Biophys Res Commun 267(1): 167-173 (2000).

Maras et al., "In vitro conversion of the carbohydrate moiety of fungal glycoproteins to mammalian-type oligosaccharides," *Eur. J. Biochem.*, 249: 701-707 (1997).

Maras et al., "*Structural characterization of N-linked* oligosaccharides from cellobiohydrolase I . . . ," *Eur. J. Biochem.*, 245: 617-625 (1997).

Maras et al., "Filamentous fungi as production organisms for glycoproteins of bio-medical interest," *Glycoconjugate Journal*, 16:99-107 (1999).

Maras et al., "Molecular Cloning and Enzymatic Characterization of a Trichoderma *reeisi* 1,2-alpha-D-mannosidase," *J. Biotechnol.*, 77(2-3):255-263, 2000.

Maras et al., "In vivo synthesis of complex N-glycans by expression of human N-acetylglucosaminyltransferase.", FEBS Letters, vol. 452, pp. 365-370 (1999).

Martinet et al., "Modification of the protein glycosylation pathway in the methylotrophic yeast *Pichia pastoris*," *Biotechnology Letters* 20(12): 1171-1177 (1998).

Maruyama et al., "A 1,2-alpha-D-Mannosidase from a Bacillus sp.: Purification, Characterization, and Mode of Action," *Carbohydrate Res.* 251:89-98 (1994).

McClure "Modeling the growth, survival and death of microorganisims in foods: the UK food micromodel approach," *Int. J. Food Microbiol.*, 23(3-4) 265-265 (1994).

McGarvey et al., "Expression of the rabies virus glycoprotein in transgenic tomatoes," *Bio-Technology* 13(13): 1484-1487 (1995).

Merkle et al., "Cloning, Expression, Purification, and Characterixation of the Murine Lysosomal Acid Alpha-Mannosidase," *Biochim Biophys Acta*, 1336(2): 132-46 (1997).

Merriam & Webster online dictionary, 2006-2007 Merriam-Webster, Incorporated, definition of "domain" pp. 1-2.

Miele et al., "Glycosylation Properties of the *Pichia pastoris*-Expressed Recombinant Kringle 2 Domain of Tissue-Type Plasminogen Activator," *Biotechnol. Appl. Biochem.*, 25:151-157 (1997).

Mimura et al., "The influence of glycosylation on the thermal stability and effector function expression of human IgG1-Fc: properties of a series of truncated glycoforms", Molecular Immunology, vol. 37, pp. 697-706 (2000).

Minowa et al., "cDNA cloning and expression of bovine UDP-N-acetylglucosamine: . . . ", J. Biol. Chem., vol. 273, pp. 11556-11562 (1998).

Moens and Vanderleyden, "Glycoproteins in prokaryotes," Arc. Microbiol. 168:169-175 (1997).

Moore and Spiro, "Characterization of the Endomannosidase Pathway for the Processing of *N*-Linked Oligosaccharides in Glucosidase II-deficient and Parent Mouse Lymphoma Cells," *J. Biol. Chem* 267(12):8443-8451 (1992).

Moremen, "Golgi α-mannosidase II deficiency in vertebrate systems: implications for asparagine-linked oligosaccharide processing in mammals," *Biochimica Biophysica Acta*, 1573: 225-235 (2002).

Moremen et al., "Biosynthesis and Modification of Golgi Mannosidase II in HeLa and 3T3 Cells," *J. Biol. Chem.*, 260(11): 6654-6662 (1985).

Moremen et al., "Topology of Mannosidase II in Rat Liver Golgi Membranes and Release of the Catalytic Domain by Selective Proteolysis," *J. Biol. Chem.*, 261(23): 10945-10951 (1986).

Moremen, "Isolation of a Rat Liver Golgi Mannosidase II Clone by Mixed Oligonucleotide-Primed Amplication of cDNA," *Proc. Natl. Acad. Sci.*, USA Jul. 1989;86(14):5276-80.

Moremen et al., "Isolation, Characterization, and Expression of cDNAs Encoding Murine ∀-Mannosidase II, a Golgi Enzyme that Controls Conversion of High Mannose to Complex N-Glycans," *Journal of Cell Biology*, Dec. 1991; 115(6):1521-34.

Moremen et al., "Glycosidases of the Asparagine-Linked Oligosaccharide Processing Pathway," *Glycobiology* 4(2): 113-125 (1994).

Morin-Ganet et al., "Morphogenesis and Dynamics of the Yeast Golgi Apparatus", Traffic, 1(1):56-68 (2000).

Nakanishi-Shindo et al., "Structure of the N-Linked Oligosaccharides That Show the Complete Loss of α-1,6-Polymannose Outer Chain from *och1, och1 mnn1*, and *och1 mnn1 alg3* Mutants in *Saccharomyces cerevisiae*," *J. Biol. Chem.*, 268(35):26338-45 (1993).

Nakayama et al., "OCHI1 Encodes a Novel Membrane Bound Mannosyltransferase: Outer Chain Elongation of Asparagine-Linked Oligosaccharides," *Embo J.*, 11(7):2511-19, 1992.

Nakayama et al. "Substrate Specificity of ∀-1,6-Mannosylatransferase that Initiates *N*-Linked Mannose Outer Chain Elongation in *Saccharomyces cerevisiae*", FEBS Lett., 412(3):547-50, 1997.

Narasimhan et al., "Control of Glycoprotein Synthesis", J. Biol. Chem., 257:10235:42 (1982).

Neiman et al., "*Saccharomyces cerevisiae* HOC1, a Supressor of pkc 1, Encodes a Putative glycosyltransferase", Genetics, 145(3):637-645 (1997).

Nikawa et al., "Structural and functional conservation of human and yeast HCP1 genese which can suppress the growth defect of the *Saccharomyces cerevisiae ire15* mutant," Gene 171(1): 107-111 (1996).

Ogawa et al., "Structure and Transcriptional Regulation of Human alpha-Mannosidase IIX (alpha-mannosidase II isotype) Gene," *Eur. J. Biochem.*, 242(3): 446-453 (1996).

Ogunjimi et al., "High-level secretory expression of immunologically active intact antibody from the yeast *Pichia pastoris*", Biotechnology Letters, 21:561-567 (1999).

Oh-eda et al., "Overexpression of the Golgi-Localized Enzyme ∀-mannosidase IIx in Chinese Hamster ovary Cells Results in the Conversion of Hexamannosyl-*N*-acetylchitobiose to Tetramannosyl-*N*-acetylchitobiose in the N-glycan-processing Pathway," *Eur. J. Biochem.*, 268: 1280-1288 (2001).

Orlandi et al., "Cloning immunolglobulin variable domains for expression by the polymerase chain reaction", Proc. Natl., Acad. Sci. USA, 86:3833 (1988).

Pakula et al., "Monitoring the kinetics of glycoprotein synthesis and secretion in the filamentous fungus *Trichoderma reesei*. . . " Microbiology, vol. 146, pp. 223-232 (2000).

Papac et al., "A high-throughput microscale method to release N-linked oligosaccharides from glycoproteins for matrix-assisted laser desorption/ionization time-of-flight mass spectrometric analysis," *Glycobiology* 8(5): 445-454 (1998).

Pearson, "Rapid and Sensitive Sequence Comparison with FASTA", Methods Enzymol. 183:63-98 (1990).

Pena, et al., "Proton pumping and the internal pH of yeast cells, measured with pyranine introduced by electroporation", Journal of Bacteriology, vol. 177, No. 4, pp. 1017-1022 (1995).

Perez et al., "Transport of Sugar Nucleotides into the Lumen of Vesicles Derived from Rat Liver Rough Endoplasmic Reticulum and Golgi Apparatus," *Methods in Enzymology*, 138: 709-715 (1987).

Puglielli et al., "Reconstitution, Identification, and Purification of the Rat Liver Golgi Membrane GDP-fucose Transporter," *J. Biol. Chem.* 274(50): 35596-35600 (1999).

Rabouille et al., "The *Drosophila GMII* Gene Enclodes Golgi α-mannosidase II," *J. Cell Sci.*, Oct. 1999;112(Pt 19): 3319-30.

Ragu et al., "Species-specific variation in glycosylation of IgG: evidence for the species-specific sialyation and branch-specific galactosylation and importance for engineering recombinant glycoprotein therapeutics", Glycobiology, 10(5):477-486 (2000).

Raju et al., "Analysis of glycoconjugates," Anal Biochem. 283(2): 123-124 (2000).

Raschke et al., "Genetic Control of Yeast Mannan Structure", J. Biol. Chem. 248(13):4660-66 (1973).

Ray et al., A Novel Glycosylation Phenotype Expressed by Lec23, a Chinese Hamster Ovary Mutant Deficient in α-Glucosidase I, *J. Biol. Chem*. 255(34):22818-22825 (1991).

Recinos et al., "Sequences of cDNAs encoding immunoglobulin heavy-and ligh-chain variable regions from two anti-dioxin monoclonal antibodies", Gene, 149:385-386 (1994).

Recinos et al., "Sequences of cDNAs encoding immunoglobulin heavy-and ligh-chain variable regions from two anti-dioxin monoclonal antibodies", Gene, 158:311-312 (1995).

Reichner et al., Recycling cell surface glycoproteins undergo limited ligosaccharide reprocessing in LEC1 mutant Chinese hamster ovary cells, Glycobiology, vol. 8, No. 12, pp. 1173-1182 (1998).

Reidhaar-Olson et al., "Combinatorial Cassett Mutagenesis as a proble of the informational content of protein sequences", Science, 241:53-57 (1988).

Ripka, et al., "Two Chinese hamster ovary glycosylation mutants affected in the conversion of GDP-mannose to GDP-fucose", Biochemistry and Biophysics, vol. 294, No. 2, pp. 533-545 (1986).

Romero et al., "Ktr1P is an ∀-1,2-mannosyltransferase of *Saccharomyces cerevisiae*," Biochem. J., 321 (Pt 2): 289-295 (1997).

Romero et al., "Mutation of Arg[273] to Leu Alters the Specificity of the Yeast *N*-Glycan Processing Class I ∀1,2-Mannosidase," *J. Biol. Chem*, 275(15):11071-11074 (2000).

Rothman et al., "Antibody-dependent cytotoxity mediated by natural killer cells is enhanced by castonospermine-induced alterations of IgG glycosylation", Molecular Immunology, vol. 26, No. 12, pp. 1113-1123 (1989).

Rothstein et al., "Targeting, Disruption, Replacement and Allele Rescue: Integrative DNA Transformation in Yeast", Methods in Enzymology, 194:281 (1991).
Ruther et al., "c-fos expression interferes with thymus development in transgenic mice," Cell 53(6): 847-856 (1988).
Sakamoto et al., Molecular Cloning and Expression of CDNA Encoding Chicken UDP-N-acetyl-D-glucosamine (GlcNAc): GlcNAc β1-6(GlcNAc β1-2)-Man α1-R[GlcNAc) to Man]β1,4N-acetylglucosaminyltransferase VI, J. Biol. Chem. vol. 275, No. 46, pp. 36029-26034 (2000).
Salovuori et al., "Low molecular weight high-mannose type glycans in a secreted protein . . . ", Bio/Technology, vol. 5, pp. 152-156 (1987).
Sambrook et al., "Hybridization of Radiolabeled Probes to immobilized nucleic acids", Molecular Cloning: A Laboratory Manual, 2d ed., Cold Spring Harbor Laboratory Press, Cold Spring Harbor, N.Y. (1989) pp. 9.51.
Sasai et al., "UDP-GlcNAc concentration is an important factor in the biosynthesis of β1,6-branched oligosaccharides: regulation based on the kinetic properties of N-acetylglucosaminytransferase V", Glycobiology, vol. 12, No. 2, pp. 119-127 (2002).
Sato et al., "Arabidopsis Thaliana DNA Chromosome 5, BAC clone F2G14 (Essa project)", XP002293613, Database accession No. AL391146, gene "F2G14_70" encoding "alpha-mannosidase-like protein" of protein_id="CACO1814.1" Abstract, Database EMBL Aug. 7, 2000.
Schachter et al., "The 'Yellow Brick Road' to Branched Complex N-glycans," Glycobiology 1(5): 453-461, 1991.
Schneikert et al., "Characterization of a Novem Mouse Recombinant Processing alpha-mannosidase," Glycobiology, 4(4):445-450 (1994).
Schwientek et al., "Golgi Localization in Yeast is Mediated by the Membrane Anchor Region in Rat Liver Sialyltransferase," J. Biol. Chem., 270(10):5483-5489 (1995).
Schwientek et al., "Golgi localization and in vivo activity of a mammalian glycosyltransferase..", J. of Biol. Chem., vol. 271, pp. 3398-3405 (1996).
Schlegel et al., XP-002293375, WO200160860-A2, Aug. 23, 2001, "Human prostate expression marker cDNA 29377".
Segawa et al., "Schizosaccharomyces pombe UDP-galatose transporter: identification of its functional form through cDNA cloning and expression in mammalian cells," FEBS Letters, 451(3): 295-298 (1999).
Shields, R. et al, "High Resolutin Mapping of the Binding Site on Human IgG1 for FcγRI, FcγRII, FcγRIII, and FcRn and Design of IgG1 Variants with improved binding to the FcγR", The Journal of Biological Chemistry, vol. 276, No. 9, pp. 6591-6604 (2001).
Shields, R. et al, "Lack of fucose on human IgG1 N-linked oligosaccharide improves binding to human FcγRIII and antibody-dependent cellular toxicity", The Journal of Biological Chemistry, vol. 277, No. 30, pp. 26733-26740 (2002).
Shiha et al., "Functional characterization of human blood coagulation factor XIa using hybridoma antibodies", J. Biol. Chem. vol. 260, No. 19, pp. 10714-10719 (1985).
Shinkawa, et al., "The Absence of Fucose but not the presence of galactose or bisecting N-Acetylglucosamine of human IgG1 complex-type oligosaccharides shows the critical role of enhancing antibody-dependent cellular cytotoxicity," The Journal of Biological Chemistry, vol. 278, No. 5, pp. 3466-3473 (2003).
Shitara, et al, "A new vector for the high level expression of chimeric antibodies in myeloma cells". Journal of Immunological Methods, vol. 167, pp. 271-278 (1994).
Sikorski et al., "A system of shuttle vectors and yeast host strains designed for efficient manipulation of DNA in Saccharomyces cerevisiae," Genetics 122(1): 19-27 (1989).
Soderholm et al. "Vector for pop-in/pop-out Gene Replacement in Pichia pastoris," Biotchniques, 31 (2):306-10 (2001).
Sommers et al., "Transport of Sugar Nucleotides into Rat Liver Golgi," J. Cell Biol., 91(2): A406-A406 (1981).
Sommers et al., "Transport of Sugar Nucleotides into Rat Liver Golgi. A New Golgi Marker Activity," J Biolog Chem, 257(18): 10811-10817 (1982).
Spiro et al., "Definition of the Lectin-like Properties of the Molecular Chaperone, Calreticulin, and Demonstration of Its Copurification with Endomannosidase from Rat Liver Golgi," J. Biol. Chem. 271(19):11588-11594 (1996).
Spiro et al., "Molecular Cloning and Expression of Rat Liver Endo-α-mannosidase, an N-linked Oligosaccharide Processing Enzyme," J. Biol. Chem. 272(46):29356-29363 (1997).
Spiro and Spiro, "Use of recombinant endomannosidase for evaluation of the processing of N-linked oligosaccharides of glycoproteins and their oligosaccharide-lipid precursors," Glycobiology 10(5):521-529 (2000).
Spiro, "Glucose residues as key determinants in the biosynthesis and quality control of glycoproteins with N-linked oligosaccharides, " Journal of Biological Chemistry, vol. 275, No. 46, pp. 35657-35660 (2000).
Spiro et al., "Glucose residues as key determinants in the biosynthesis and quality control . . . ," J. Biol. Chem., vol. 275, pp. 35657-35660 (2000).
Spiro et al., "Molecular cloning and expression of rat liver endo-α-mannosidase . . . ," J. Biol. Chem., vol. 272, pp. 29356-29363 (1997).
Strasser et al., "Molecular basis of N-acetylglucosaminyltransferase I deficiency", Biochem. J., vol. 387, pp. 385-391 (2005).
Stanely et al., "Complementation between mutants of CHO cells resistant to a variety of plant lectins", Somatic Cell Genet 3(4):391-405 (1977).
Staub et al., "High-yield production of a human therapeutic protein in tobacco chloroplasts," Nature Biotechnology 18(3): 333-338 (2000).
Stix, "Supercharging Protein Manufacture," Scientific Amer., vol. 290, pp. 32-33 (2004).
Suzuki et al., "Characterizaion of alpha-1,6-mannosyltransferase responsible for the synthesis of branched side chains in candida albicans mannan.", Eur J. Biochem, vol. 240, No. 1, pp. 37-44, (1996).
Svetina et al., "Expression of Catalytic Subunit of Bovine Enterokinase in the Filamentous Fungus Aspergillus niger," J. Biotechnol., 76(2-3): 245-251 (2000).
Swarnakar et al., XP-002293374, WO200297060-A2, Dec. 5, 2002, "Novel human carbohydrate associated polypeptide, useful in diagnosis, treatment and prevention . . . ".
Swiss Prot P11655, dated Oct. 1989.
Swiss Prot P32906, dated Oct. 1993.
Swiss Prot P39107, dated Feb. 1995.
Swiss Prot P50108, dated Oct. 1996.
Swiss Prot P53008, dated Oct. 1996.
Swarnakar et al., XP-002293374, WO200297060-A2, Dec. 5, 2002, "Novel human carbohydrate associated polypeptide, useful in diagnosis, treatment and prevention . . . ,".
Takeuchi, "Trial for molecular breeding of yeast for the production of glycoprotein therapeutics," Trends in Glycoscience and Glycotechnology 9:S29-S35 (1997).
Tang et al., XP-002293372, WO2003025148-A2, Mar. 27, 2003, "New Polynucleotides and secreted proteins, useful for treating myeloid or lymphoid cell disorders . . . ".
Tang et al., XP-002293373, WO2003025148-A2, Mar. 27, 2003, "New Polynucleotides and secreted proteins, useful for treating myeloid or lymphoid cell disorders . . . ".
Tatara et al., J. of Biol. Chem., vol. 278 (2003), pp. 25289-25294, "Identification of catalytic residues of Ca2+-independent . . . ".
Teixeira et al. (2005) Antifungal susceptibility and pathogenic potential of environmental isolated filamentous fungi compared with colonizing agents in immunocompromised patients. Mycopathologia., vol. 160, No. 2, pp. 129-135.
Terness et al., "Idiotypic vaccine for treatment of human B-cell lymphoma", Hum. Immunol., 56:17-27 (1997).
Tremblay et al., "Cloning and expression of a specific human α1,2-mannosidase that trims Man9GlcNac2 to Man8GlcNac2 isomer B during N-glycan biosynthesis", Glycobiology, vol. 9, No. 10, pp. 1073-1078 (1999).
Tremblay et al., "Characterization of a cDNA encoding a novel human Golgi α1,2-Mannosidase (IC) involved in N-Glycan Biosynthesis,"The Journal of Biological Chemistry, vol. 275, No. 41, pp. 31655-31660 (2000).

Tremblay et al., "Molecular cloning, chromosomal mapping and tissue-specific expression of a novel human α-1,2-mannosidase gene involved in N-glycan maturation", Glycobiology, 8(6):585-595 (1998).

Tsuji-Hayashi et al., "A potential endogenous ligand of annexin IV in the Exocrine pancreas", The Journal of Biological Chemistry, 277(49):47493-47499 (2002).

Tsujikawa et al., "Secretion of a variant of human single—chain urokinase-type plasminogen activator without an N-glycosylation site in the methylotrophic yeast, Pichia patoris and characterization of the secreted product:", Yeast, vol. 12, No. 6, pp. 541-553 (1996).

Umana et al., "Tetracycline-Regulated Overexpression of glycosyltransferase in Chinese hamster ovary cells", Biotechnol. Bioeng., 65(5):542-549 (1999).

Umaña et al., "Engineered Glycoforms of an Antineuroblastoma IgG1 with Optimized Antibody-Dependent Cellular Cytotoxic Activity," Nature Biotechnology, 17(1):176-80 (1999).

Vervecken et al., "In vivo synthesis of mammalian-like . . . ", Appl. Environ. Microbiol., vol. 70, pp. 2639-2646 (2004).

Voet et al., Biochemistry, John Wiley & Sons (1990), pp. 266-267, Section 10-3. Glycoproteins.

Ware et al., "Expression of Human Platelet Glycoprotein Ib-Alpha in Transgenic Mice," Thrombosis and Haemostasis 69(6): 1194-1194 (1993).

Weikert et al., "Engineering Chinese Hamster Ovary Cells to Maximize Sialic Acid Content of Recombinant Glycoproteins", Nature Biotechnology, 17(11): 1116-1121, Nov. 1999.

Weng et al., "Evaluation of the early processing routes of N-linked oligosaccharides of glycoproteins through the characterization of Man GlcNAc2 . . . ", Glycobiology, vol. 6, pp. 861-868 (1996).

Welschof et al., "Amino acid sequence based PCR primers for amplification of rearranged human heavy and light chain immunolglobulin variable region genes", J. Immunol. Methods, 179:203-214 (1995).

Werner et al., "Appropriate Mammalian Expression Systems for Biopharmaceuticals," Arzneimittelforschung, Aug. 1998;48(8):870-80.

Wikipidia (2008, updated) Signla Peptide, en-wikipedia.org/wiki/signal_peptide, pp. 1-3.

Wildt et al., "The Humanization of N-Glycosylation Pathways in Yeast", Nat. Rev. Microbiol., vol. 3, No. 2, pp. 119-128 (2005).

Wiggins et al., "Activity of the yeast MNN1 alpha-1,3-mannosyltransferase requires a notif conserved in many other families of glycosyltransfereases," Proc. Nat. Acad. Sci. USA 95(14): 7945-7950 (1998).

Xie, et al., "Direct demonstration of MuSK involvement in acetylcholine receptor clustering through identification of agonist ScFv", Nature Biotechnology, vol. 15, pp. 768-771 (1997).

Yamane-Ohnuki et al., "Establishment of FUT8 knockout Chinese hamster ovary cells: An ideal host cel line for producing . . . ", Biotech, Bioengin., vol. 87, pp. 614-622 (2004).

Yang et al., "Glycosylation and proteolytic processing of 70 kDa C-terminal recombinant polypeptides of Plasmodium falciparum merozoite surface protein 1 expressed in mammalian cells," Glycobiology, 9(12): (1999) 1347-55.

Yang et al., "Effects of Ammonia on CHO Cell Growth, Erythropoietin Production, and Glycosylation", Biotechnol Bioeng., 68(4): 370-80 (2000).

Yip et al., "Cloning and analysis of the Saccharomyces cerevisiae MNN9 and MNN1 genes required for complex glycosylation of secreted proteins," Proc. Natl. Acad. Sci. USA, 91(7): 2723-2727 (1994).

Yoko-o et al., "Schizosaccharomyces pombe Och1(+) Encodes Alpha-1,6-Mannosyltranferase that is involved in Outer Chain Elongation of N-Linked Oligosaccharides," FEBS Lett., 489(1): 75-80 (2001).

Yoshida et al., "1-2-alpha-D-mannosidase from Penicillium citriunum: molecular and enzymic properties of two isoenzymes," Biochem. J. 290 (Pt2): 349-354 (1993).

Yoshida et al., "Expression and charaterization of rat UDP-N-acetylgluocosamine: α-3-D-mannoside β-1,2-N-acetylglucosaminyltransferase I in Saccharomyces cerevisiae," Glycobiology, 9 (1): 53-58 (1999).

Yoshida et al., "Molecular cloning and nucleotide sequence of the genomic DNA for 1-2-alpha-D-mannosidase gene, msdC from Penicillium citriunum," Biochem. Biophys. Acta. vol. 1263, No. 2 pp. 159-162 (1995).

Zerangue et al, "Analysis of endoplasmic reticulum trafficking singals by combinatorial screening in mammalian cells", Proc. Natl. Acad. Sci. USA, vol. 98, No. 5, pp. 2431-2436 (2001).

Zhang and Madden, "PowerBLAST: a new network BLAST application for interactive or automated sequence analysis and annotation", Genome Res. 7:649-656 (1997).

Zhu et al., "Structural studies of alpha-N-acetylgalactosaminidase: Effect of glycosylation..", Archives of Biochem. & Biophysics, vol. 352, pp. 1-8 (1998).

Zuber et al., "Golgi Apparatus Immunolocalization of Endomannosidase Suggests Post-Endoplasmic Reticulum Glucose Trimming: Implications for Quality Control," Mol. Bio. of the Cell, 11:4227-4240 (2000).

Genbank Accession No. NM 00528, dated Sep. 25, 2005.
Genbank Accession No. AF005034, dated Jul. 10, 1997.
Genbank Accession No. AF106080, dated Apr. 17, 1999.
Genbank Accession No. AK116684, dated Nov. 30, 2002.
Genbank Accession No. D55649, dated Feb. 7, 2003.
Genbank Accession No. NM_073594, dated Aug. 19, 2005.
Genbank Accession No. NM_121499, dated Nov. 4, 2005.
Genbank Accession No. U31520, dated Dec. 13, 1995.
Genbank Accession No. X77652, dated Apr. 24, 1995.
Genbank Accession No. XM_218816, dated Apr. 24, 1995.
Genbank Accession No. NM 002406, dated Sep. 23, 2005.
Genbank Accession No. CAA98114, dated Aug. 9, 2005.
Genbank Accession No. NM_088548 (Genbank AN 6678787), dated Apr. 7, 2003.
Genbank Accession No. NM006715, dated Oct. 18, 2005.
Genbank Accession No. X61172, dated Apr. 18, 2005.

Opposition Brief filed by Novozymes A/S for EP1297172 B1 (English Translation) (2005).

Opposition Brief filed (French) by Glycode SAS for EP1297172 B1 (English Translation) (2006).

Opposition Brief filed by Glycode SAS for EP1297172 B1 (English Translation) (2006).

Preliminary EPO non-binding opinion of the opposition division for EP1297172 B1 (2007).

Pantentee's Reply to the Notice of Opposition for EP1297172 B1 (2007).

Applicants response of Apr. 18, 2008 to Office Action re U.S. Appl. No. 11/187,066.

Applicants response to Apr. 11, 2008 to Office Action re U.S. Appl. No. 11/187,196.

Appliants response to Apr. 11, 2008 to Office Action re U.S. Appl. No. 11/187,113.

Opposition Brief filed by Novartis against EP1597379 (Feb. 15, 2010).

Opposition Brief filed by Novozymes A/S for EP1297172 B1 (2007).

Further submission by Patentee in opposition proceeding against EP 1297172B1 (2007).

Opinion of the Opposition Division for EP1297172B1 (2007).

Grounds of Appeal for EP 1297172 B1 (2008).

Response by Glycode to Grounds of Appeal for EP 1297172 B1 (2008) (English Translation of French Document).

Preliminary Opinion of Appeal Board for EP 1297171 B1 (2010).

O'Brian et al., "Mass Spectrometry of Cardiac Calsequestrin Characterizes Microheterogeneity Unique to Heart and Indicative of Complex Intracellular Transit", The Journal of Biological Chemistry, vol. 277, No. 40, pp. 37154-37160 (2002).

* cited by examiner

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:

-continued

<223> OTHER INFORMATION: Primer A for target gene in P. pastoris
      (1,6-mannosyltransferase)

<400> SEQUENCE: 1
atggcgaagg cagatggcag t                                             21

<210> SEQ ID NO 2
<211> LENGTH: 21
<212> TYPE: DNA
<213> ORGANISM: Artificial Sequence
<220> FEATURE:
<223> OTHER INFORMATION: Primer B for target gene in P. pastoris
      (1,6-mannosyltransferase)

<400> SEQUENCE: 2
ttagtccttc caacttcctt c                                             21

<210> SEQ ID NO 3
<211> LENGTH: 26
<212> TYPE: DNA
<213> ORGANISM: Artificial Sequence
<220> FEATURE:
<223> OTHER INFORMATION: Primer A for target gene in P. pastoris (1,2
      mannosyltransferases)
<220> FEATURE:
<221> NAME/KEY: misc_feature
<222> LOCATION: 3
<223> OTHER INFORMATION: n=c or t
<220> FEATURE:
<221> NAME/KEY: misc_feature
<222> LOCATION: 7
<223> OTHER INFORMATION: n=a or c
<220> FEATURE:
<221> NAME/KEY: misc_feature
<222> LOCATION: 9
<223> OTHER INFORMATION: n=a, t, g, or c
<220> FEATURE:
<221> NAME/KEY: misc_feature
<222> LOCATION: 12
<223> OTHER INFORMATION: n=a, t, g, or c
<220> FEATURE:
<221> NAME/KEY: misc_feature
<222> LOCATION: 15
<223> OTHER INFORMATION: n=a or g
<220> FEATURE:
<221> NAME/KEY: misc_feature
<222> LOCATION: (17)...(17)
<223> OTHER INFORMATION: n=c or t
<220> FEATURE:
<221> NAME/KEY: misc_feature
<222> LOCATION: (18)...(18)
<223> OTHER INFORMATION: n=a, t, c, or g
<220> FEATURE:
<221> NAME/KEY: misc_feature
<222> LOCATION: (21)...(21)
<223> OTHER INFORMATION: n=c or t
<220> FEATURE:
<221> NAME/KEY: misc_feature
<222> LOCATION: (24)...(24)
<223> OTHER INFORMATION: n=a, c, or t

<400> SEQUENCE: 3
tantggngng tngancnnga natnaa                                        26

<210> SEQ ID NO 4
<211> LENGTH: 20
<212> TYPE: DNA
<213> ORGANISM: Artificial Sequence
<220> FEATURE:
<223> OTHER INFORMATION: Primer B for target gene in P. pastoris (1,2
      mannosyltransferases)
<220> FEATURE:
<221> NAME/KEY: misc_feature
<222> LOCATION: 3

```
<223> OTHER INFORMATION: n=a or g
<220> FEATURE:
<221> NAME/KEY: misc_feature
<222> LOCATION: 6
<223> OTHER INFORMATION: n=a, t, g, or c
<220> FEATURE:
<221> NAME/KEY: misc_feature
<222> LOCATION: 12
<223> OTHER INFORMATION: n=a, t, g, or c
<220> FEATURE:
<221> NAME/KEY: misc_feature
<222> LOCATION: 14
<223> OTHER INFORMATION: n=g or t
<220> FEATURE:
<221> NAME/KEY: misc_feature
<222> LOCATION: 15
<223> OTHER INFORMATION: n=c or t
<220> FEATURE:
<221> NAME/KEY: misc_feature
<222> LOCATION: (18)...(18)
<223> OTHER INFORMATION: n=a or g

<400> SEQUENCE: 4 gcntcnccccc ancnntcnta                                          20

<210> SEQ ID NO 5
<211> LENGTH: 4
<212> TYPE: PRT
<213> ORGANISM: Artificial Sequence
<220> FEATURE:
<223> OTHER INFORMATION: Signal tetrapeptide

<400> SEQUENCE: 5

His Asp Glu Leu
1

<210> SEQ ID NO 6
<211> LENGTH: 4
<212> TYPE: PRT
<213> ORGANISM: Artificial Sequence
<220> FEATURE:
<223> OTHER INFORMATION: Signal tetrapeptide

<400> SEQUENCE: 6

Lys Asp Glu Leu
1
```

METHODS FOR PRODUCING MODIFIED GLYCOPROTEINS

CROSS REFERENCE TO RELATED APPLICATIONS

This application is a divisional application of U.S. Ser. No. 11/271,235, filed Nov. 10, 2005, now issued U.S. Pat. No. 7,629,163, which is a divisional application of U.S. Ser. No. 09/892,591, filed Jun. 27, 2001, now issued U.S. Pat. No. 7,029,872, which claims the benefit of U.S. Provisional Application Ser. No. 60/214,358, filed on Jun. 28, 2000, U.S. Provisional Application Ser. No. 60/215,638, filed Jun. 30, 2000, and U.S. Provisional Application Ser. No. 60/279,997, filed on Mar. 30, 2001.

STATEMENT OF FEDERALLY SPONSORED RESEARCH

This invention was made with government support under Phase I SBIR grant no. 1R43GM66690-1 from the National Institute of Health (NIH) and the National Institute of General Medical Sciences (NIGMS) and grant no. 70NANB2H3046 from the National Institute of Standards and Technology Advanced Technology Program (NIST-ATP).

REFERENCE TO SEQUENCE LISTING SUBMITTED ELECTRONICALLY

The sequence listing of the present application is submitted electronically via EFS-Web as an ASCII formatted sequence listing with a file name "GF0021YDCDA-SEQTXT-26 AUG2009.txt", creation date of Aug. 26, 2009, and a size of 44.0 KB. This sequence listing submitted via EFS-Web is part of the specification and is herein incorporated by reference in its entirety.

FIELD OF THE INVENTION

The present invention is directed to methods and compositions by which fungi or other eukaryotic microorganisms can be genetically modified to produce glycosylated proteins (glycoproteins) having patterns of glycosylation similar to glycoproteins produced by animal cells, especially human cells, which are useful as human or animal therapeutic agents.

BACKGROUND OF THE INVENTION

Glycosylation Pathways

De novo synthesized proteins may undergo further processing in cells, known as post-translational modification. In particular, sugar residues may be added enzymatically, a process known as glycosylation. The resulting proteins bearing covalently linked oligosaccharide side chains are known as glycosylated proteins or glycoproteins. Bacteria typically do not glycosylate proteins; in cases where glycosylation does occur it usually occurs at nonspecific sites in the protein (Moens and Vanderleyden, Arch. Microbiol. 1997 168(3): 169-175).

Eukaryotes commonly attach a specific oligosaccharide to the side chain of a protein asparagine residue, particularly an asparagine which occurs in the sequence Asn-Xaa-Ser/Thr/Cys (where Xaa represents any amino acid). Following attachment of the saccharide moiety, known as an N-glycan, further modifications may occur in vivo. Typically these modifications occur via an ordered sequence of enzymatic reactions, known as a cascade. Different organisms provide different glycosylation enzymes (glycosyltransferases and glycosidases) and different glycosyl substrates, so that the final composition of a sugar side chain may vary markedly depending upon the host.

For example, microorganisms such as filamentous fungi and yeast (lower eukaryotes) typically add additional mannose and/or mannosylphosphate sugars. The resulting glycan is known as a "high-mannose" type or a mannan. By contrast, in animal cells, the nascent oligosaccharide side chain may be trimmed to remove several mannose residues and elongated with additional sugar residues that typically do not occur in the N-glycans of lower eukaryotes. See R. K. Bretthauer, et al. *Biotechnology and Applied Biochemistry*, 1999, 30, 193-200; W. Martinet, et al. *Biotechnology Letters*, 1998, 20, 1171-1177; S. Weikert, et al. *Nature Biotechnology*, 1999, 17, 1116-1121; M. Malissard, et al. *Biochemical and Biophysical Research Communications*, 2000, 267, 169-173; Jarvis, et al. 1998 Engineering N-glycosylation pathways in the baculovirus-insect cell system, Current Opinion in Biotechnology, 9:528-533; and M. Takeuchi, 1997 *Trends in Glycoscience and Glycotechnology*, 1997, 9, S29-S35.

The N-glycans that are produced in humans and animals are commonly referred to as complex N-glycans. A complex N-glycan means a structure with typically two to six outer branches with a sialyllactosamine sequence linked to an inner core structure $Man_3GlcNAc_2$. A complex N-glycan has at least one branch, and preferably at least two, of alternating GlcNAc and galactose (Gal) residues that terminate in oligosaccharides such as, for example: NeuNAc-; NeuAcα2-6GalNAcα1-; NeuAcα2-3Galβ1-3GalNAcα1-; NeuAcα2-3/6Galβ1-4GlcNAcβ1-; GlcNAcα1-4Galβ1-(mucins only); Fucα1-2Galβ1-(blood group H). Sulfate esters can occur on galactose, GalNAc, and GlcNAc residues, and phosphate esters can occur on mannose residues. NeuAc (Neu: neuraminic acid; Ac:acetyl) can be O-acetylated or replaced by NeuGl (N-glycolylneuraminic acid). Complex N-glycans may also have intrachain substitutions of bisecting GlcNAc and core fucose (Fuc).

Human glycosylation begins with a sequential set of reactions in the endoplasmatic reticulum (ER) leading to a core oligosaccharide structure, which is transferred onto de novo synthesized proteins at the asparagine residue in the sequence Asn-Xaa-Ser/Thr (see FIG. 1A). Further processing by glucosidases and mannosidases occurs in the ER before the nascent glycoprotein is transferred to the early Golgi apparatus, where additional mannose residues are removed by Golgi-specific 1,2-mannosidases. Processing continues as the protein proceeds through the Golgi. In the medial Golgi a number of modifying enzymes including N-acetylglucosamine transferases (GnT I, GnT II, GnT III, GnT IV, GnT V, GnT VI), mannosidase II, fucosyltransferases add and remove specific sugar residues (see FIG. 1B). Finally in the trans Golgi, the N-glycans are acted on by galactosyl transferases and sialyltransferases (ST) and the finished glycoprotein is released from the Golgi apparatus. The protein N-glycans of animal glycoproteins have bi-, tri-, or tetra-antennary structures, and may typically include galactose, fucose, and N-acetylglucosamine. Commonly the terminal residues of the N-glycans consist of sialic acid. A typical structure of a human N-glycan is shown in FIG. 1B.

Sugar Nucleotide Precursors

The N-glycans of animal glycoproteins typically include galactose, fucose, and terminal sialic acid. These sugars are not generally found on glycoproteins produced in yeast and filamentous fungi. In humans, the full range of nucleotide sugar precursors (e.g. UDP-N-acetylglucosamine, UDP-N-acetylgalactosamine, CMP-N-acetylneuraminic acid, UDP-galactose, GDP-fucose etc.) are generally synthesized in the cytosol and transported into the Golgi, where they are attached to the core oligosaccharide by glycosyltransferases. (Sommers and Hirschberg, 1981 *J. Cell Biol.* 91(2): A406-A406; Sommers and Hirschberg 1982 *J. Biol. Chem.* 257(18): 811-817; Perez and Hirschberg 1987 *Methods in Enzymology* 138: 709-715.

Glycosyl transfer reactions typically yield a side product which is a nucleoside diphosphate or monophosphate. While monophosphates can be directly exported in exchange for nucleoside triphosphate sugars by an antiport mechanism, diphosphonucleosides (e.g. GDP) have to be cleaved by phosphatases (e.g. GDPase) to yield nucleoside monophosphates and inorganic phosphate prior to being exported. This reaction is important for efficient glycosylation; for example, GDPase from *S. cerevisiae* has been found to be necessary for mannosylation. However the GDPase has 90% reduced activity toward UDP (Berninsone et al., 1994 J. Biol. Chem. 269 (1):207-211α). Lower eukaryotes typically lack UDP-specific diphosphatase activity in the Golgi since they do not utilize UDP-sugar precursors for Golgi-based glycoprotein synthesis. *Schizosaccharomyces pombe*, a yeast found to add galactose residues to cell wall polysaccharides (from UDP-galactose) has been found to have specific UDPase activity, indicating the requirement for such an enzyme (Beminsone et al., 1994). UDP is known to be a potent inhibitor of glycosyltransferases and the removal of this glycosylation side product is important in order to prevent glycosyltransferase inhibition in the lumen of the Golgi (Khatara et al., 1974). See Beminsone, P., et al. 1995. *J. Biol. Chem.* 270(24): 14564-14567; Beaudet, L., et al. 1998 *Abc Transporters: Biochemical, Cellular, and Molecular Aspects.* 292: 397-413.

Compartmentalization of Glycosylation Enzymes

Glycosyltransferases and mannosidases line the inner (luminal) surface of the $ER^X$ and Golgi apparatus and thereby provide a catalytic surface that allows for the sequential processing of glycoproteins as they proceed through the ER and Golgi network. The multiple compartments of the cis, medial, and trans Golgi and the trans Golgi Network (TGN), provide the different localities in which the ordered sequence of glycosylation reactions can take place. As a glycoprotein proceeds from synthesis in the ER to full maturation in the late Golgi or TGN, it is sequentially exposed to different glycosidases, mannosidases and glycosyltransferases such that a specific N-glycan structure may be synthesized. The enzymes typically include a catalytic domain, a stem region, a membrane spanning region and an N-terminal cytoplasmic tail. The latter three structural components are responsible for directing a glycosylation enzyme to the appropriate locus.

Localization sequences from one organism may function in other organisms. For example the membrane spanning region of α-2,6-sialyltransferase (α-2,6-ST) from rats, an enzyme known to localize in the rat trans Golgi, was shown to also localize a reporter gene (invertase) in the yeast Golgi (Schwientek, et al., 1995). However, the very same membrane spanning region as part of a full-length of α-2,6-sialyltransferase was retained in the ER and not further transported to the Golgi of yeast (Krezdorn et al., 1994). A full length GalT from humans was not even synthesized in yeast, despite demonstrably high transcription levels. On the other hand the transmembrane region of the same human GalT fused to an invertase reporter was able to direct localization to the yeast Golgi, albeit it at low production levels. Schwientek and co-workers have shown that fusing 28 amino acids of a yeast mannosyltransferase (Mnt1), a region containing an N-terminal cytoplasmic tail, a transmembrane region and eight amino acids of the stem region, to the catalytic domain of human GalT are sufficient for Golgi localization of an active GalT (Schwientek et al. 1995 J. Biol. Chem. 270(10):5483-5489). Other galactosyltransferases appear to rely on interactions with enzymes resident in particular organelles since after removal of their transmembrane region they are still able to localize properly.

Improper localization of a glycosylation enzyme may prevent proper functioning of the enzyme in the pathway. For example *Aspergillus nidulans*, which has numerous α-1,2-mannosidases (Eades and Hintz, 2000 Gene 255(1):25-34), does not add GlcNAc to $Man_5GlcNAc_2$ when transformed with the rabbit GnT I gene, despite a high overall level of GnT I activity (Kalsner et al., 1995). GnT I, although actively expressed, may be incorrectly localized such that the enzyme is not in contact with both of its substrates: the nascent N-glycan of the glycoprotein and UDP-GlcNAc. Alternatively, the host organism may not provide an adequate level of UDP-GlcNAc in the Golgi.

Glycoproteins Used Therapeutically

A significant fraction of proteins isolated from humans or other animals are glycosylated. Among proteins used therapeutically, about 70% are glycosylated. If a therapeutic protein is produced in a microorganism host such as yeast, however, and is glycosylated utilizing the endogenous pathway, its therapeutic efficiency is typically greatly reduced. Such glycoproteins are typically immunogenic in humans and show a reduced half-life in vivo after administration (Takeuchi, 1997).

Specific receptors in humans and animals can recognize terminal mannose residues and promote the rapid clearance of the protein from the bloodstream. Additional adverse effects may include changes in protein folding, solubility, susceptibility to proteases, trafficking, transport, compartmentalization, secretion, recognition by other proteins or factors, antigenicity, or allergenicity. Accordingly, it has been necessary to produce therapeutic glycoproteins in animal host systems, so that the pattern of glycosylation is identical or at least similar to that in humans or in the intended recipient species. In most cases a mammalian host system, such as mammalian cell culture, is used.

Systems for Producing Therapeutic Glycoproteins

In order to produce therapeutic proteins that have appropriate glycoforms and have satisfactory therapeutic effects, animal or plant-based expression systems have been used. The available systems include:

1. Chinese hamster ovary cells (CHO), mouse fibroblast cells and mouse myeloma cells (Arzneimittelforschung. 1998 August; 48(8):870-880);
2. Transgenic animals such as goats, sheep, mice and others (Dente Prog. Clin. Biol. 1989 Res. 300:85-98, Ruther et al., 1988 Cell 53(6):847-856; Ware, J., et al. 1993 *Thrombosis* and *Haemostasis* 69(6): 1194-1194; Cole, E. S., et al. 1994 *J.Cell.Biochem.* 265-265);
3. Plants (*Arabidopsis thaliana*, tobacco etc.) (Staub, et al. 2000 *Nature Biotechnology* 18(3): 333-338) (McGarvey, P. B., et al. 1995 *Bio-Technology* 13(13): 1484-1487; Bardor, M., et al. 1999 *Trends in Plant Science* 4(9): 376-380);
4. Insect cells (*Spodoptera frugiperda* Sf9, Sf21, *Trichoplusia ni*, etc. in combination with recombinant baculoviruses such as *Autographa californica* multiple nuclear polyhedrosis virus which infects lepidopteran cells) (Altmans et al., 1999 Glycoconj. J. 16(2):109-123).

Recombinant human proteins expressed in the above-mentioned host systems may still include non-human glycoforms (Raju et al., 2000 Annals Biochem. 283(2): 123-132). In particular, fraction of the N-glycans may lack terminal sialic acid, typically found in human glycoproteins. Substantial efforts have been directed to developing processes to obtain glycoproteins that are as close as possible in structure to the human forms, or have other therapeutic advantages. Glycoproteins having specific glycoforms may be especially useful, for example in the targeting of therapeutic proteins. For example, the addition of one or more sialic acid residues to a glycan side chain may increase the lifetime of a therapeutic glycoprotein in vivo after administration. Accordingly, the mammalian host cells may be genetically engineered to increase the extent of terminal sialic acid in glycoproteins expressed in the cells. Alternatively sialic acid may be conjugated to the protein of interest in vitro prior to administration using a sialic acid transferase and an appropriate substrate. In addition, changes in growth medium composition or the expression of enzymes involved in human glycosylation have been employed to produce glycoproteins more closely resembling the human forms (S. Weikert, et al., *Nature Biotechnology*, 1999, 17, 1116-1121; Werner, Noe, et al 1998 Arzneimittelforschung 48(8):870-880; Weikert, Papac et al., 1999; Andersen and Goochee 1994 *Cur. Opin. Biotechnol.* 5: 546-549; Yang and Butler 2000 *Biotechnol. Bioengin.* 68(4): 370-380). Alternatively cultured human cells may be used.

However, all of the existing systems have significant drawbacks. Only certain therapeutic proteins are suitable for expression in animal or plant systems (e.g. those lacking in any cytotoxic effect or other effect adverse to growth). Animal and plant cell culture systems are usually very slow, frequently requiring over a week of growth under carefully controlled conditions to produce any useful quantity of the protein of interest. Protein yields nonetheless compare unfavorably with those from microbial fermentation processes. In addition cell culture systems typically require complex and expensive nutrients and cofactors, such as bovine fetal serum. Furthermore growth may be limited by programmed cell death (apoptosis).

Moreover, animal cells (particularly mammalian cells) are highly susceptible to viral infection or contamination. In some cases the virus or other infectious agent may compromise the growth of the culture, while in other cases the agent may be a human pathogen rendering the therapeutic protein product unfit for its intended use. Furthermore many cell culture processes require the use of complex, temperature-sensitive, animal-derived growth media components, which may carry pathogens such as bovine spongiform encephalopathy (BSE) prions. Such pathogens are difficult to detect and/or difficult to remove or sterilize without compromising the growth medium. In any case, use of animal cells to produce therapeutic proteins necessitates costly quality controls to assure product safety.

Transgenic animals may also be used for manufacturing high-volume therapeutic proteins such as human serum albumin, tissue plasminogen activator, monoclonal antibodies, hemoglobin, collagen, fibrinogen and others. While transgenic goats and other transgenic animals (mice, sheep, cows, etc.) can be genetically engineered to produce therapeutic proteins at high concentrations in the milk, the process is costly since every batch has to undergo rigorous quality control. Animals may host a variety of animal or human pathogens, including bacteria, viruses, fungi, and prions. In the case of scrapies and bovine spongiform encephalopathy, testing can take about a year to rule out infection. The production of therapeutic compounds is thus preferably carried out in a well-controlled sterile environment, e.g. under Good Manufacturing Practice (GMP) conditions. However, it is not generally feasible to maintain animals in such environments. Moreover, whereas cells grown in a fermenter are derived from one well characterized Master Cell Bank (MCB), transgenic animal technology relies on different animals and thus is inherently non-uniform. Furthermore external factors such as different food uptake, disease and lack of homogeneity within a herd, may effect glycosylation patterns of the final product. It is known in humans, for example, that different dietary habits result in differing glycosylation patterns.

Transgenic plants have been developed as a potential source to obtain proteins of therapeutic value. However, high level expression of proteins in plants suffers from gene silencing, a mechanism by which the genes for highly expressed proteins are down-regulated in subsequent plant generations. In addition, plants add xylose and/or α-1,3-linked fucose to protein N-glycans, resulting in glycoproteins that differ in structure from animals and are immunogenic in mammals (Altmann, Marz et al., 1995 Glycoconj. J. 12(2); 150-155). Furthermore, it is generally not practical to grow plants in a sterile or GMP environment, and the recovery of proteins from plant tissues is more costly than the recovery from fermented microorganisms.

Glycoprotein Production Using Eukaryotic Microorganisms

The lack of a suitable expression system is thus a significant obstacle to the low-cost and safe production of recombinant human glycoproteins. Production of glycoproteins via the fermentation of microorganisms would offer numerous advantages over the existing systems. For example, fermentation-based processes may offer (a) rapid production of high concentrations of protein; (b) the ability to use sterile, well-controlled production conditions (e.g. GMP conditions); (c) the ability to use simple, chemically defined growth media; (d) ease of genetic manipulation; (e) the absence of contaminating human or animal pathogens; (f) the ability to express a wide variety of proteins, including those poorly expressed in cell culture owing to toxicity etc.; (g) ease of protein recovery (e.g. via secretion into the medium). In addition, fermentation facilities are generally far less costly to construct than cell culture facilities.

As noted above, however, bacteria, including species such as *Escherichia coli* commonly used to produce recombinant proteins, do not glycosylate proteins in a specific manner like eukaryotes. Various methylotrophic yeasts such as *Pichia pastoris, Pichia methanolica*, and *Hansenula polymorpha*, are particularly useful as eukaryotic expression systems, since they are able to grow to high cell densities and/or secrete large quantities of recombinant protein. However, as noted above, glycoproteins expressed in these eukaryotic microorganisms differ substantially in N-glycan structure from those in animals. This has prevented the use of yeast or filamentous fungi as hosts for the production of many useful glycoproteins.

Several efforts have been made to modify the glycosylation pathways of eukaryotic microorganisms to provide glycoproteins more suitable for use as mammalian therapeutic agents. For example, several glycosyltransferases have been separately cloned and expressed in *S. cerevisiae* (GalT, GnT I), *Aspergillus nidulans* (GnT I) and other fungi (Yoshida et al., 1999, Kalsner et al., 1995 Glycoconj. J. 12(3):360-370, Schwientek et al., 1995). However, N-glycans with human characteristics were not obtained.

Yeasts produce a variety of mannosyltransferases e.g. 1,3-mannosyltransferases (e.g. MNN1 in *S. cerevisiae*) (Graham and Emr, 1991 J. Cell. Biol. 114(2):207-218), 1,2-mannosyltransferases (e.g. KTR/KRE family from *S. cerevisiae*), 1,6-mannosyltransferases (OCH1 from *S. cerevisiae*), mannosylphosphate transferases (MNN4 and MNN6 from *S. cerevisiae*) and additional enzymes that are involved in endogenous glycosylation reactions. Many of these genes have been deleted individually, giving rise to viable organisms having altered glycosylation profiles. Examples are shown in Table 1.

TABLE 1

Examples of yeast strains having altered mannosylation

| Strain | N-glycan (wild type) | Mutation | N-glycan (mutant) | Reference |
|---|---|---|---|---|
| S. pombe | $Man_{>9}GlcNAc_2$ | OCH1 | $Man_8GlcNAc_2$ | Yoko-o et al., 2001 FEBS Lett. 489(1): 75-80 |
| S. cerevisiae | $Man_{>9}GlcNAc_2$ | OCH1/MNN1 | $Man_8GlcNAc_2$ | Nakanishi-Shindo et al,. 1993 J. Biol. Chem. 268(35): 26338-26345 |
| S. cerevisiae | $Man_{>9}GlcNAc_2$ | OCH1/MNN1/MNN4 | $Man_8GlcNAc_2$ | Chiba et al., 1998 J. Biol. Chem. 273, 26298-26304 |

In addition, Japanese Patent Application Public No. 8-336387 discloses an OCH1 mutant strain of *Pichia pastoris*. The OCH1 gene encodes 1,6-mannosyltransferase, which adds a mannose to the glycan structure $Man_8GlcNAc_2$ to yield $MangGlcNAc_2$. The $MangGlcNAc_2$ structure is then a substrate for further mannosylation in vivo, leading to the hypermannosylated glycoproteins that are characteristic of yeasts and typically may have at least 30-40 mannose residue per N-glycan. In the OCH1 mutant strain, proteins glycosylated with $Man_8GlcNAc_2$ are accumulated and hypermannosylation does not occur. However, the structure $Man_8GlcNAc_2$ is not a substrate for animal glycosylation enzymes, such as human UDP-GlcNAc transferase I, and accordingly the method is not useful for producing proteins with human glycosylation patterns.

Martinet et al. (Biotechnol. Lett. 1998, 20(12), 1171-1177) reported the expression of α-1,2-mannosidase from *Trichoderma reesei* in *P. pastoris*. Some mannose trimming from the N-glycans of a model protein was observed. However, the model protein had no N-glycans with the structure $Man_5GlcNAc_2$, which would be necessary as an intermediate for the generation of complex N-glycans. Accordingly the method is not useful for producing proteins with human or animal glycosylation patterns.

Similarly, Chiba et al. 1998 expressed α-1,2-mannosidase from *Aspergillus saitoi* in the yeast *Saccharomyces cerevisiae*. A signal peptide sequence (His-Asp-Glu-Leu) was engineered into the exogenous mannosidase to promote retention in the endoplasmic reticulum. In addition, the yeast host was a mutant lacking three enzyme activities associated with hypermannosylation of proteins: 1,6-mannosyltransferase (OCH1); 1,3-mannosyltransferase (MNN1); and mannosylphosphatetransferase (MNN4). The N-glycans of the triple mutant host thus consisted of the structure $Man_8GlcNAc_2$, rather than the high mannose forms found in wild-type *S. cerevisiae*. In the presence of the engineered mannosidase, the N-glycans of a model protein (carboxypeptidase Y) were trimmed to give a mixture consisting of 27 mole % $Man_5GlcNAc_2$, 22 mole % $Man_6GlcNAc_2$, 22 mole % $Man_7GlcNAc_2$, 29 mole % $Man_8GlcNAc_2$. Trimming of the endogenous cell wall glycoproteins was less efficient, only 10 mole % of the N-glycans having the desired $Man_5GlcNAc_2$ structure.

Since only the $Man_5GlcNAc_2$ glycans would be susceptible to further enzymatic conversion to human glycoforms, the method is not efficient for the production of proteins having human glycosylation patterns. In proteins having a single N-glycosylation site, at least 73 mole % would have an incorrect structure. In proteins having two or three N-glycosylation sites, respectively at least 93 or 98 mole % would have an incorrect structure. Such low efficiencies of coversion are unsatisfactory for the production of therapeutic agents, particularly as the separation of proteins having different glycoforms is typically costly and difficult.

With the object of providing a more human-like glycoprotein derived from a fungal host, U.S. Pat. No. 5,834,251 to Maras and Contreras discloses a method for producing a hybrid glycoprotein derived from *Trichoderma reesei*. A hybrid N-glycan has only mannose residues on the Manα1-6 arm of the core and one or two complex antennae on the Manα1-3 arm. While this structure has utility, the method has the disadvantage that numerous enzymatic steps must be performed in vitro, which is costly and time-consuming. Isolated enzymes are expensive to prepare and maintain, may need unusual and costly substrates (e.g. UDP-GlcNAc), and are prone to loss of activity and/or proteolysis under the conditions of use.

It is therefore an object of the present invention to provide a system and methods for humanizing glycosylation of recombinant glycoproteins expressed in *Pichia pastoris* and other lower eukaryotes such as *Hansenula polymorpha*, *Pichia stiptis*, *Pichia methanolica*, *Pichia* sp, *Kluyveromyces* sp, *Candida albicans*, *Aspergillus nidulans*, and *Trichoderma reseei*.

SUMMARY OF THE INVENTION

Cell lines having genetically modified glycosylation pathways that allow them to carry out a sequence of enzymatic reactions, which mimic the processing of glycoproteins in humans, have been developed. Recombinant proteins expressed in these engineered hosts yield glycoproteins more similar, if not substantially identical, to their human counterparts. The lower eukaryotes, which ordinarily produce high-mannose containing N-glycans, including unicellular and multicellular fungi such as *Pichia pastoris*, *Hansenula polymorpha*, *Pichia stiptis*, *Pichia methanolica*, *Pichia* sp., *Kluyveromyces* sp., *Candida albicans*, *Aspergillus nidulans*, and *Trichoderma reseei*, are modified to produce N-glycans such as $Man_5GlcNAc_2$ or other structures along human glycosylation pathways. This is achieved using a combination of engineering and/or selection of strains which: do not express certain enzymes which create the undesirable complex structures characteristic of the fungal glycoproteins, which express exogenous enzymes selected either to have optimal activity under the conditions present in the fungi where activity is desired, or which are targeted to an organelle where optimal activity is achieved, and combinations thereof wherein the genetically engineered eukaryote expresses multiple exogenous enzymes required to produce "human-like" glycoproteins.

In a first embodiment, the microorganism is engineered to express an exogenous α-1,2-mannosidase enzyme having an optimal pH between 5.1 and 8.0, preferably between 5.9 and 7.5. In an alternative preferred embodiment, the exogenous enzyme is targeted to the endoplasmic reticulum or Golgi apparatus of the host organism, where it trims N-glycans such as $Man_8GlcNAc_2$ to yield $Man_5GlcNAc_2$. The latter structure is useful because it is identical to a structure formed in mammals, especially humans; it is a substrate for further glycosylation reactions in vivo and/or in vitro that produce a finished N-glycan that is similar or identical to that formed in mammals, especially humans; and it is not a substrate for hypermannosylation reactions that occur in vivo in yeast and other microorganisms and that render a glycoprotein highly immunogenic in animals.

In a second embodiment, the glycosylation pathway of an eukaryotic microorganism is modified by (a) constructing a DNA library including at least two genes encoding exogenous glycosylation enzymes; (b) transforming the microorganism with the library to produce a genetically mixed population expressing at least two distinct exogenous glycosylation enzymes; (c) selecting from the population a microorganism having the desired glycosylation phenotype. In a preferred embodiment, the DNA library includes chimeric genes each encoding a protein localization sequence and a catalytic activity related to glycosylation. Organisms modified using the method are useful for producing glycoproteins having a glycosylation pattern similar or identical to mammals, especially humans.

In a third embodiment, the glycosylation pathway is modified to express a sugar nucleotide transporter enzyme. In a preferred embodiment, a nucleotide diphosphatase enzyme is also expressed. The transporter and diphosphatase improve the efficiency of engineered glycosylation steps, by providing the appropriate substrates for the glycosylation enzymes in the appropriate compartments, reducing competitive product inhibition, and promoting the removal of nucleoside diphosphates.

DETAILED DESCRIPTION OF THE INVENTION

Figure 1A:
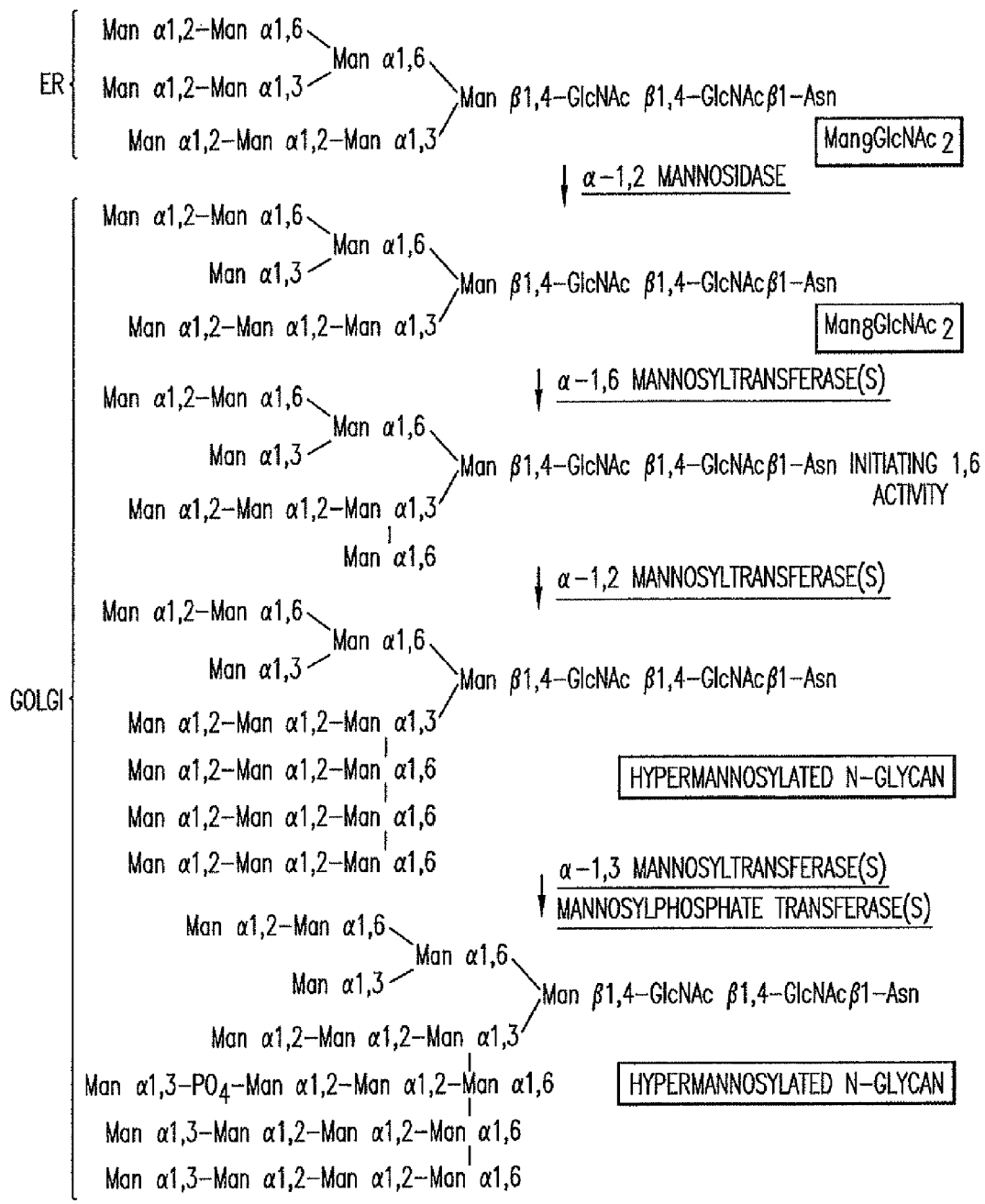
FIG. 1A is a schematic diagram of typical fungal N-glycosylation pathway.

The methods and recombinant lower eukaryotic strains described herein are used to make "humanized glycoproteins". The recombinant lower eukaryotes are made by engineering lower eukaryotes which do not express one or more enzymes involved in production of high mannose structures to express the enzymes required to produce human-like sugars. As used herein, a lower eukaryote is a unicellular or filamentous fungus. As used herein, a "humanized glycoprotein" refers to a protein having attached thereto N-glycans including less than four mannose residues, and the synthetic intermediates (which are also useful and can be manipulated further in vitro) having at least five mannose residues. In a preferred embodiment, the glycoproteins produced in the recombinant lower eukaryotic strains contain at least 27 mole % of the Man5 intermediate. This is achieved by cloning in a better mannosidase, i.e., an enzyme selected to have optimal activity under the conditions present in the organisms at the site where proteins are glycosylated, or by targeting the enzyme to the organelle where activity is desired.

In a preferred embodiment, eukaryotic strains which do not express one or more enzymes involved in the production of high mannose structures are used. These strains can be engineered or one of the many such mutants already described in yeasts, including a hypermannosylation-minus (OCH1) mutant in *Pichia pastoris*.

The strains can be engineered one enzyme at a time, or a library of genes encoding potentially useful enzymes can be created, and those strains having enzymes with optimal activities or producing the most "human-like" glycoproteins, selected.

Lower eukaryotes that are able to produce glycoproteins having the attached N-glycan $Man_5GlcNAc_2$ are particularly useful since (a) lacking a high degree of mannosylation (e.g. greater than 8 mannoses per N-glycan, or especially 30-40 mannoses), they show reduced immunogenicity in humans; and (b) the N-glycan is a substrate for further glycosylation reactions to form an even more human-like glycoform, e.g. by the action of GlcNAc transferase I to form $GlcNAcMan_5GlcNAc_2$. $Man_5GlcNAc_2$ must be formed in vivo in a high yield, at least transiently, since all subsequent glycosylation reactions require $Man_5GlcNAc_2$ or a derivative thereof. Accordingly, a yield is obtained of greater than 27 mole %, more preferably a yield of 50-100 mole %, glycoproteins in which a high proportion of N-glycans have $Man_5GlcNAc_2$. It is then possible to perform further glycosylation reactions in vitro, using for example the method of U.S. Pat. No. 5,834,251 to Maras and Contreras. In a preferred embodiment, at least one further glycosylation reaction is performed in vivo. In a highly preferred embodiment thereof, active forms of glycosylating enzymes are expressed in the endoplasmic reticulum and/or Golgi apparatus.

Host Microorganisms

Yeast and filamentous fungi have both been successfully used for the production of recombinant proteins, both intracellular and secreted (Cereghino, J. L. and J. M. Cregg 2000 *FEMS Microbiology Reviews* 24(1): 45-66; Harkki, A., et al. 1989 *Bio-Technology* 7(6): 596; Berka, R. M., et al. 1992 *Abstr. Papers Amer. Chem. Soc.* 203: 121-BIOT; Svetina, M., et al. 2000 *J. Biotechnol.* 76(2-3): 245-251.

Figure 1B:
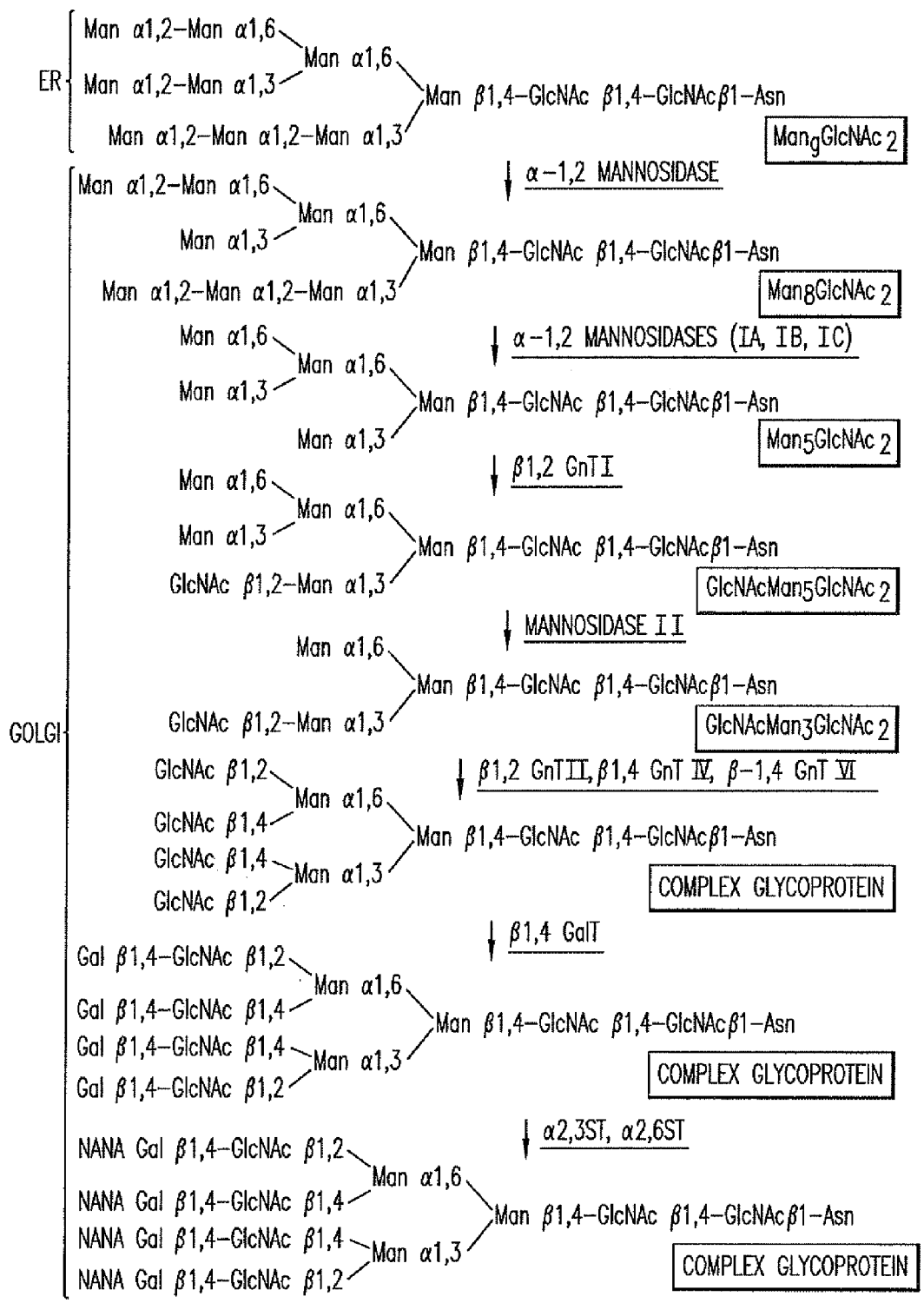
FIG. 1B is a schematic diagram of a typical human N-glycosylation pathway.

Although glycosylation in yeast and fungi is very different than in humans, some common elements are shared. The first step, the transfer of the core oligosaccharide structure to the nascent protein, is highly conserved in all eukaryotes including yeast, fungi, plants and humans (compare FIGS. 1A and 1B). Subsequent processing of the core oligosaccharide, however, differs significantly in yeast and involves the addition of several mannose sugars. This step is catalyzed by mannosyltransferases residing in the Golgi (e.g. OCH1, MNT1, MNN1, etc.), which sequentially add mannose sugars to the core oligosaccharide. The resulting structure is undesirable for the production of humanoid proteins and it is thus desirable to reduce or eliminate mannosyl transferase activity. Mutants of *S. cerevisiae*, deficient in mannosyl transferase activity (e.g. och1 or mnn9 mutants) have shown to be nonlethal and display a reduced mannose content in the oligosaccharide of yeast glycoproteins. Other oligosaccharide processing enzymes, such as mannosylphophate transferase may also have to be eliminated depending on the host's particular endogenous glycosylation pattern. After reducing undesired endogenous glycosylation reactions the formation of complex N-glycans has to be engineered into the host system. This requires the stable expression of several enzymes and sugar-nucleotide transporters. Moreover, one has to locate these enzymes in a fashion such that a sequential processing of the maturing glycosylation structure is ensured.

Target Glycoproteins

The methods described herein are useful for producing glycoproteins, especially glycoproteins used therapeutically in humans. Such therapeutic proteins are typically administered by injection, orally, pulmonary, or other means.

Examples of suitable target glycoproteins include, without limitation: erythropoietin, cytokines such as interferon-α, interferon-β, interferon-γ, interferon-ω, and granulocyte-CSF, coagulation factors such as factor VIII, factor IX, and human protein C, soluble IgE receptor α-chain, IgG, IgM, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, and osteoprotegerin.

Method for Producing Glycoproteins Comprising the N-Glycan $Man_5GlcNAc_2$

The first step involves the selection or creation of a lower eukaryote that is able to produce a specific precursor structure of $Man_5GlcNAc_2$, which is able to accept in vivo GlcNAc by the action of a GlcNAc transferase I. This step requires the formation of a particular isomeric structure of $Man_5GlcNAc_2$. This structure has to be formed within the cell at a high yield (in excess of 30%) since all subsequent manipulations are contingent on the presence of this precursor. $Man_5GlcNAc_2$ structures are necessary for complex N-glycan formation, however, their presence is by no means sufficient, since $Man_5GlcNAc_2$ may occur in different isomeric forms, which may or may not serve as a substrate for GlcNAc transferase I. Most glycosylation reactions are not complete and thus a particular protein generally contains a range of different carbohydrate structures (i.e. glycoforms) on its surface. The mere presence of trace amounts (less than 5%) of a particular structure like $Man_5GlcNAc_2$ is of little practical relevance. It is the formation of a particular, GlcNAc transferase I accepting intermediate (Structure I) in high yield (above 30%), which is required. The formation of this intermediate is necessary and subsequently allows for the in vivo synthesis of complex N-glycans.

One can select such lower eukaryotes from nature or alternatively genetically engineer existing fungi or other lower eukaryotes to provide the structure in vivo. No lower eukaryote has been shown to provide such structures in vivo in excess of 1.8% of the total N-glycans (Maras et al., 1997), so a genetically engineered organism is preferred. Methods such as those described in U.S. Pat. No. 5,595,900, may be used to identify the absence or presence of particular glycosyltransferases, mannosidases and sugar nucleotide transporters in a target organism of interest.

Inactivation of Fungal Glycosylation Enzymes Such as 1,6-Mannosyltransferase

The method described herein may be used to engineer the glycosylation pattern of a wide range of lower eukaryotes (e.g. *Hansenula polymorpha, Pichia stiptis, Pichia methanolica, Pichia* sp, *Kluyveromyces* sp, *Candida albicans, Aspergillus nidulans, Trichoderma reseei* etc.). *Pichia pastoris* is used to exemplify the required manipulation steps. Similar to other lower eukaryotes, *P. pastoris* processes $Man_9GlcNAc_2$ structures in the ER with a 1,2-α-mannosidase to yield $Man_8GlcNAc_2$. Through the action of several mannosyltransferases, this structure is then converted to hypermannosylated structures ($Man_{>9}GlcNAc_2$), also known as mannans. In addition, it has been found that *P. pastoris* is able to add non-terminal phosphate groups, through the action of mannosylphosphate transferases to the carbohydrate structure. This is contrary to the reactions found in mammalian cells, which involve the removal of mannose sugars as opposed to their addition. It is of particular importance to eliminate the ability of the fungus to hypermannosylate the existing $Man_8GlcNAc_2$ structure. This can be achieved by either selecting for a fungus that does not hypermannosylate, or by genetically engineering such a fungus.

Genes that are involved in this process have been identified in *Pichia pastoris* and by creating mutations in these genes one is able to reduce the production of "undesirable" glycoforms. Such genes can be identified by homology to existing mannosyltransferases (e.g. OCH1, MNN4, MNN6, MNN1), found in other lower eukaryotes such as *C. albicans, Pichia angusta* or *S. cerevisiae* or by mutagenizing the host strain and selecting for a phenotype with reduced mannosylation. Based on homologies amongst known mannosyltransferases and mannosylphosphate transferases, one may either design PCR primers, examples of which are shown in Table 2, or use genes or gene fragments encoding such enzymes as probes to identify homologues in DNA libraries of the target organism. Alternatively, one may be able to complement particular phenotypes in related organisms. For example, in order to obtain the gene or genes encoding 1,6-mannosyltransferase activity in *P. pastoris*, one would carry out the following steps. OCH1 mutants of *S. cerevisiae* are temperature sensitive and are slow growers at elevated temperatures. One can thus identify functional homologues of OCH1 in *P. pastoris* by complementing an OCH1 mutant of *S. cerevisiae* with a *P. pastoris* DNA or cDNA library. Such mutants of *S. cerevisiae* may be found e.g., see the *Saccharomyces* genome link at the Stanford University website and are commercially available. Mutants that display a normal growth phenotype at elevated temperature, after having been transformed with a *P. pastoris* DNA library, are likely to carry an OCH1 homologue of *P. pastoris*. Such a library can be created by partially digesting chromosomal DNA of *P. pastoris* with a suitable restriction enzyme and after inactivating the restriction enzyme ligating the digested DNA into a suitable vector, which has been digested with a compatible restriction enzyme. Suitable vectors are pRS314, a low copy (CEN6/ARS4) plasmid based on pBluescript containing the Trp1 marker (Sikorski, R. S., and Hieter, P., 1989, Genetics 122, pg 19-27) or pFL44S, a high copy (2µ) plasmid based on a modified pUC19 containing the URA3 marker (Bonneaud, N., et al., 1991, Yeast 7, pg. 609-615). Such vectors are commonly used by academic researchers or similar vectors are available from a number of different vendors such as Invitrogen (Carlsbad, Calif.), Pharmacia (Piscataway, N.J.), New England Biolabs (Beverly, Mass.). Examples are pYES/GS, 2µ origin of replication based yeast expression plasmid from Invitrogen, or Yep24 cloning vehicle from New England Biolabs. After ligation of the chromosomal DNA and the vector one may transform the DNA library into strain of *S. cerevisiae* with a specific mutation and select for the correction of the corresponding phenotype. After sub-cloning and sequencing the DNA fragment that is able to restore the wild-type phenotype, one may use this fragment to eliminate the activity of the gene product encoded by OCH1 in *P. pastoris*.

Alternatively, if the entire genomic sequence of a particular fungus of interest is known, one may identify such genes simply by searching publicly available DNA databases, which are available from several sources such as NCBI, Swissprot etc. For example by searching a given genomic sequence or data base with a known 1,6 mannosyltransferase gene (OCH1) from *S. cerevisiae*, one can able to identify genes of high homology in such a genome, which a high degree of certainty encodes a gene that has 1,6 mannosyltransferase activity. Homologues to several known mannosyltransferases from *S. cerevisiae* in *P. pastoris* have been identified using either one of these approaches. These genes have similar functions to genes involved in the mannosylation of proteins in *S. cerevisiae* and thus their deletion may be used to manipulate the glycosylation pattern in *P. pastoris* or any other fungus with similar glycosylation pathways.

The creation of gene knock-outs, once a given target gene sequence has been determined, is a well-established technique in the yeast and fungal molecular biology community, and can be carried out by anyone of ordinary skill in the art (R. Rothsteins, (1991) Methods in Enzymology, vol. 194, p. 281). In fact, the choice of a host organism may be influenced by the availability of good transformation and gene disruption techniques for such a host. If several mannosyltransferases have to be knocked out, the method developed by Alani and Kleckner allows for the repeated use of the URA3 markers to sequentially eliminate all undesirable endogenous mannosyltransferase activity. This technique has been refined by others but basically involves the use of two repeated DNA sequences, flanking a counter selectable marker. For example: URA3 may be used as a marker to ensure the selection of a transformants that have integrated a construct. By flanking the URA3 marker with direct repeats one may first select for transformants that have integrated the construct and have thus disrupted the target gene. After isolation of the transformants, and their characterization, one may counter select in a second round for those that are resistant to 5'FOA. Colonies that able to survive on plates containing 5'FOA have lost the URA3 marker again through a crossover event involving the repeats mentioned earlier. This approach thus allows for the repeated use of the same marker and facilitates the disruption of multiple genes without requiring additional markers.

Eliminating specific mannosyltransferases, such as 1,6 mannosyltransferase (OCH1), mannosylphosphate transferases (MNN4, MNN6, or genes complementing lbd mutants) in *P. pastoris*, allows for the creation of engineered strains of this organism which synthesize primarily $Man_8GlcNAc_2$ and thus can be used to further modify the glycosylation pattern to more closely resemble more complex human glycoform structures. A preferred embodiment of this method utilizes known DNA sequences, encoding known biochemical glycosylation activities to eliminate similar or identical biochemical functions in *P. pastoris*, such that the glycosylation structure of the resulting genetically altered *P. pastoris* strain is modified.

TABLE 2

| PCR primer A | PCR primer B | Target Gene(s) in P. pastoris | Homologues |
|---|---|---|---|
| ATGGCGAAGGCA GATGGCAGT (SEQ ID NO: 1) | TTAGTCCTTCCA ACTTCCTTC (SEQ ID NO: 2) | 1,6-mannosyl-transferase | OCH1 S. cerevisiae, Pichia albicans |

TABLE 2-continued

| PCR primer A | PCR primer B | Target Gene(s) in P. pastoris | Homologues |
|---|---|---|---|
| TAYTGGMGNGTN GARCYNGAYATH AA (SEQ ID NO: 3) | GCRTCNCCCCAN CKYTCRTA (SEQ ID NO: 4) | 1,2 mannosyl-transferases | KTR/KRE family, S. cerevisiae |

Legend: M = A or C, R = A or G, W = A or T, S = C or G, Y = C or T, K = G or T, V = A or C or G, H = A or C or T, D = A or G or T, B = C or G or T, N = G or A or T or C.

Incorporation of a Mannosidase into the Genetically Engineered Host

The process described herein enables one to obtain such a structure in high yield for the purpose of modifying it to yield complex N-glycans. A successful scheme to obtain suitable $Man_5GlcNAc_2$ structures must involve two parallel approaches: (1) reducing endogenous mannosyltransferase activity and (2) removing 1,2-α-mannose by mannosidases to yield high levels of suitable $Man_5GlcNAc_2$ structures. What distinguishes this method from the prior art is that it deals directly with these two issues. As the work of Chiba and coworkers demonstrates, one can reduce $Man_8GlcNAc_2$ structures to a $Man_5GlcNAc_2$ isomer in *S. cerevisiae*, by engineering the presence of a fungal mannosidase from *A. saitoi* into the ER. The shortcomings of their approach are twofold: (1) insufficient amounts of $Man_5GlcNAc_2$ are formed in the extra-cellular glycoprotein fraction (10%) and (2) it is not clear that the in vivo formed $Man_5GlcNAc_2$ structure in fact is able to accept GlcNAc by action of GlcNAc transferase I. If several glycosylation sites are present in a desired protein the probability (P) of obtaining such a protein in a correct form follows the relationship $P=(F)^n$, where n equals the number of glycosylation sites, and F equals the fraction of desired glycoforms. A glycoprotein with three glycosylation sites would have a 0.1% chance of providing the appropriate precursors for complex and hybrid N-glycan processing on all of its glycosylation sites, which limits the commercial value of such an approach.

Most enzymes that are active in the ER and Golgi apparatus of *S. cerevisiae* have pH optima that are between 6.5 and 7.5 (see Table 3). All previous approaches to reduce mannosylation by the action of recombinant mannosidases have concentrated on enzymes that have a pH optimum around pH 5.0 (Martinet et al., 1998, and Chiba et al., 1998), even though the activity of these enzymes is reduced to less than 10% at pH 7.0 and thus most likely provide insufficient activity at their point of use, the ER and early Golgi of *P. pastoris* and *S. cerevisiae*. A preferred process utilizes an α-mannosidase in vivo, where the pH optimum of the mannosidase is within 1.4 pH units of the average pH optimum of other representative marker enzymes localized in the same organelle(s). The pH optimum of the enzyme to be targeted to a specific organelle should be matched with the pH optimum of other enzymes found in the same organelle, such that the maximum activity per unit enzyme is obtained. Table 3 summarizes the activity of mannosidases from various sources and their respective pH optima. Table 4 summarizes their location.

TABLE 3

Mannosidases and their pH optimum.

| Source | Enzyme | pH optimum | Reference |
|---|---|---|---|
| *Aspergillus saitoi* | 1,2-α-mannosidase | 5.0 | Ichishima et al., 1999 Biochem. J. 339 (Pt 3): 589-597 |
| *Trichoderma reesei* | 1,2-α-mannosidase | 5.0 | Maras et al., 2000 J. Biotechnol. 77(2-3): 255-263 |

TABLE 3-continued

Mannosidases and their pH optimum.

| Source | Enzyme | pH optimum | Reference |
|---|---|---|---|
| *Penicillium citrinum* | 1,2-α-D-mannosidase | 5.0 | Yoshida et al., 1993 Biochem. J. 290 (Pt 2): 349-354 |
| *Aspergillus nidulans* | 1,2-α-mannosidase | 6.0 | Eades and Hintz, 2000 |
| *Homo sapiens* IA (Golgi) | 1,2-α-mannosidase | 6.0 | |
| *Homo sapiens* IB (Golgi) | 1,2-α-mannosidase | 6.0 | |
| *Lepidopteran* insect cells | Type I 1,2-α-Man$_6$-mannosidase | 6.0 | Ren et al., 1995 Biochem. 34(8): 2489-2495 |
| *Homo sapiens* | α-D-mannosidase | 6.0 | Chandrasekaran et al., 1984 Cancer Res. 44(9): 4059-68 |
| *Xanthomonas manihotis* | 1,2,3-α-mannosidase | 6.0 | |
| Mouse IB (Golgi) | 1,2-α-mannosidase | 6.5 | Schneikert and Herscovics, 1994 Glycobiology. 4(4): 445-50 |
| *Bacillus* sp. (secreted) | 1,2-α-D-mannosidase | 7.0 | Maruyama et al., 1994 Carbohydrate Res. 251: 89-98 |

When one attempts to trim high mannose structures to yield Man$_5$GlcNAc$_2$ in the ER or the Golgi apparatus of *S. cerevisiae*, one may choose any enzyme or combination of enzymes that (1) has/have a sufficiently close pH optimum (i.e. between pH 5.2 and pH 7.8), and (2) is/are known to generate, alone or in concert, the specific isomeric Man$_5$GlcNAc$_2$ structure required to accept subsequent addition of GlcNAc by GnT I. Any enzyme or combination of enzymes that has/have shown to generate a structure that can be converted to GlcNAcMan$_5$GlcNAc$_2$ by GnT I in vitro would constitute an appropriate choice. This knowledge may be obtained from the scientific literature or experimentally by determining that a potential mannosidase can convert Man$_8$GlcNAc$_2$-PA to Man$_5$GlcNAc$_2$-PA and then testing, if the obtained Man$_5$GlcNAc$_2$-PA structure can serve a substrate for GnT I and UDP-GlcNAc to give GlcNAcMan$_5$GlcNAc$_2$ in vitro. For example, mannosidase IA from a human or murine source would be an appropriate choice.

1,2-Mannosidase Activity in the ER and Golgi

Previous approaches to reduce mannosylation by the action of cloned exogenous mannosidases have failed to yield glycoproteins having a sufficient fraction (e.g. >27 mole %) of N-glycans having the structure Man$_5$GlcNAc$_2$ (Martinet et al., 1998, and Chiba et al., 1998). These enzymes should function efficiently in ER or Golgi apparatus to be effective in converting nascent glycoproteins. Whereas the two mannosidases utilized in the prior art (from *A. saitoi* and *T. reesei*) have pH optima of 5.0, most enzymes that are active in the ER and Golgi apparatus of yeast (e.g. *S. cerevisiae*) have pH optima that are between 6.5 and 7.5 (see Table 3). Since the glycosylation of proteins is a highly evolved and efficient process, it can be concluded that the internal pH of the ER and the Golgi is also in the range of about 6-8. At pH 7.0, the activity of the mannosidases used in the prior art is reduced to less than 10%, which is insufficient for the efficient production of Man$_5$GlcNAc$_2$ in vivo.

TABLE 4

Cellular location and pH optima of various glycosylation-related enzymes of *S. cerevisiae*.

| Gene | Activity | Location | pH optimum | Author(s) |
|---|---|---|---|---|
| Ktr1 | α-1,2 mannosyltransferase | Golgi | 7.0 | Romero et al., 1997 Biochem. J. 321 (Pt 2): 289-295 |
| Mns1 | α-1,2-mannosidase | ER | 6.5 | |
| CWH41 | glucosidase I | ER | 6.8 | |
| — | mannosyltransferase | Golgi | 7-8 | Lehele and Tanner, 1974 Biochim. Biophys. Acta 350(1): 225-235 |
| Kre2 | α-1,2 mannosyltransferase | Golgi | 6.5-9.0 | Romero et al., 1997 |

The α-1,2-mannosidase enzyme should have optimal activity at a pH between 5.1 and 8.0. In a preferred embodiment, the enzyme has an optimal activity at a pH between 5.9 and 7.5. The optimal pH may be determined under in vitro assay conditions. Preferred mannosidases include those listed in Table 3 having appropriate pH optima, e.g. *Aspergillus nidulans*, *Homo sapiens* IA (Golgi), *Homo sapiens* IB (Golgi), Lepidopteran insect cells (IPLB-SF21AE), *Homo sapiens*, mouse IB (Golgi), and *Xanthomonas manihotis*. In a preferred embodiment, a single cloned mannosidase gene is expressed in the host organism. However, in some cases it may be desirable to express several different mannosidase genes, or several copies of one particular gene, in order to achieve adequate production of Man$_5$GlcNAc$_2$. In cases where multiple genes are used, the encoded mannosidases should all have pH optima within the preferred range of 5.1 to 8.0, or especially between 5.9 and 7.5. In an especially preferred embodiment mannosidase activity is targeted to the ER or cis Golgi, where the early reactions of glycosylation occur.

Formation of Complex N-Glycans

A second step of the process involves the sequential addition of sugars to the nascent carbohydrate structure by engineering the expression of glucosyltransferases into the Golgi apparatus. This process first requires the functional expression of GnT I in the early or medial Golgi apparatus as well as ensuring the sufficient supply of UDP-GlcNAc.

Integration Sites

Since the ultimate goal of this genetic engineering effort is a robust protein production strain that is able to perform well in an industrial fermentation process, the integration of multiple genes into the fungal chromosome involves careful planning. The engineered strain will most likely have to be transformed with a range of different genes, and these genes will have to be transformed in a stable fashion to ensure that the desired activity is maintained throughout the fermentation process. Any combination of the following enzyme activities will have to be engineered into the fungal protein expression host: sialyltransferases, mannosidases, fucosyltransferases, galactosyltransferases, glucosyltransferases, GlcNAc transferases, ER and Golgi specific transporters (e.g. syn and antiport transporters for UDP-galactose and other precursors), other enzymes involved in the processing of oligosaccharides, and enzymes involved in the synthesis of activated oligosaccharide precursors such as UDP-galactose, CMP-N-acetylneuraminic acid. At the same time a number of genes which encode enzymes known to be characteristic of non-human glycosylation reactions, will have to be deleted.

Targeting of Glycosyltransferases to Specific Organelles:

Glycosyltransferases and mannosidases line the inner (luminal) surface of the ER and Golgi apparatus and thereby provide a "catalytic" surface that allows for the sequential processing of glycoproteins as they proceed through the ER and Golgi network. In fact the multiple compartments of the cis, medial, and trans Golgi and the trans-Golgi Network (TGN), provide the different localities in which the ordered sequence of glycosylation reactions can take place. As a glycoprotein proceeds from synthesis in the ER to full maturation in the late Golgi or TGN, it is sequentially exposed to different glycosidases, mannosidases and glycosyltransferases such that a specific carbohydrate structure may be synthesized. Much work has been dedicated to revealing the exact mechanism by which these enzymes are retained and anchored to their respective organelle. The evolving picture is complex but evidence suggests that stem region, membrane spanning region and cytoplasmic tail individually or in concert direct enzymes to the membrane of individual organelles and thereby localize the associated catalytic domain to that locus.

Targeting sequences are well known and described in the scientific literature and public databases, as discussed in more detail below with respect to libraries for selection of targeting sequences and targeted enzymes.

Method for Producing a Library to Produce Modified Glycosylation Pathways

A library including at least two genes encoding exogeneous glycosylation enzymes is transformed into the host organism, producing a genetically mixed population. Transformants having the desired glycosylation phenotypes are then selected from the mixed population. In a preferred embodiment, the host organism is a yeast, especially *P. pastoris*, and the host glycosylation pathway is modified by the operative expression of one or more human or animal glycosylation enzymes, yielding protein N-glycans similar or identical to human glycoforms. In an especially preferred embodiment, the DNA library includes genetic constructs encoding fusions of glycosylation enzymes with targeting sequences for various cellular loci involved in glycosylation especially the ER, cis Golgi, medial Golgi, or trans Golgi.

Examples of modifications to glycosylation which can be effected using method are: (1) engineering an eukaryotic microorganism to trim mannose residues from $Man_8GlcNAc_2$ to yield $Man_5GlcNAc_2$ as a protein N-glycan; (2) engineering an eukaryotic microorganism to add an N-acetylglucosamine (GlcNAc) residue to $Man_5GlcNAc_2$ by action of GlcNAc transferase I; (3) engineering an eukaryotic microorganism to functionally express an enzyme such as an N-acetylglucosamine transferase (GnT I, GnT II, GnT III, GnT IV, GnT V, GnT VI), mannosidase II, fucosyltransferase, galactosyl tranferase (GalT) or sialyltransferases (ST).

By repeating the method, increasingly complex glycosylation pathways can be engineered into the target microorganism. In one preferred embodiment, the host organism is transformed two or more times with DNA libraries including sequences encoding glycosylation activities. Selection of desired phenotypes may be performed after each round of transformation or alternatively after several transformations have occurred. Complex glycosylation pathways can be rapidly engineered in this manner.

DNA Libraries

It is necessary to assemble a DNA library including at least two exogenous genes encoding glycosylation enzymes. In addition to the open reading frame sequences, it is generally preferable to provide each library construct with such promoters, transcription terminators, enhancers, ribosome binding sites, and other functional sequences as may be necessary to ensure effective transcription and translation of the genes upon transformation into the host organism. Where the host is *Pichia pastoris*, suitable promoters include, for example, the AOX1, AOX2, DAS, and P40 promoters. It is also preferable to provide each construct with at least one selectable marker, such as a gene to impart drug resistance or to complement a host metabolic lesion. The presence of the marker is useful in the subsequent selection of transformants; for example, in yeast the URA3, HIS4, SUC2, G418, BLA, or SH BLE genes may be used.

In some cases the library may be assembled directly from existing or wild-type genes. In a preferred embodiment however the DNA library is assembled from the fusion of two or more sub-libraries. By the in-frame ligation of the sub-libraries, it is possible to create a large number of novel genetic constructs encoding useful targeted glycosylation activities. For example, one useful sub-library includes DNA sequences encoding any combination of enzymes such as sialyltransferases, mannosidases, fucosyltransferases, galactosyltransferases, glucosyltransferases, and GlcNAc transferases. Preferably, the enzymes are of human origin, although other mammalian, animal, or fungal enzymes are also useful. In a preferred embodiment, genes are truncated to give fragments encoding the catalytic domains of the enzymes. By removing endogenous targeting sequences, the enzymes may then be redirected and expressed in other cellular loci. The choice of such catalytic domains may be guided by the knowledge of the particular environment in which the catalytic domain is subsequently to be active. For example, if a particular glycosylation enzyme is to be active in the late Golgi, and all known enzymes of the host organism in the late Golgi have a certain pH optimum, then a catalytic domain is chosen which exhibits adequate activity at that pH.

Another useful sub-library includes DNA sequences encoding signal peptides that result in localization of a protein to a particular location within the ER, Golgi, or trans Golgi network. These signal sequences may be selected from the host organism as well as from other related or unrelated organisms. Membrane-bound proteins of the ER or Golgi typically may include, for example, N-terminal sequences encoding a cytosolic tail (ct), a transmembrane domain (tmd), and a stem region (sr). The ct, tmd, and sr sequences are sufficient individually or in combination to anchor proteins to the inner (lumenal) membrane of the organelle. Accordingly, a preferred embodiment of the sub-library of signal sequences includes ct, tmd, and/or sr sequences from these proteins. In some cases it is desirable to provide the sub-library with varying lengths of sr sequence. This may be accomplished by PCR using primers that bind to the 5' end of the DNA encoding the cytosolic region and employing a series of opposing primers that bind to various parts of the stem region. Still other useful sources of signal sequences include retrieval signal peptides, e.g. the tetrapeptides HDEL (SEQ ID NO:5) or KDEL (SEQ ID NO:6), which are typically found at the C-terminus of proteins that are transported retrograde into the ER or Golgi. Still other sources of signal sequences include (a) type II membrane proteins, (b) the enzymes listed in Table 3, (c) membrane spanning nucleotide sugar transporters that are localized in the Golgi, and (d) sequences referenced in Table 5.

TABLE 5

Sources of useful compartmental targeting sequences

| Gene or Sequence | Organism | Function | Location of Gene Product |
|---|---|---|---|
| MnsI | S. cerevisiae | α-1,2-mannosidase | ER |
| OCH1 | S. cerevisiae | 1,6-mannosyltransferase | Golgi (cis) |
| MNN2 | S. cerevisiae | 1,2-mannosyltransferase | Golgi (medial) |
| MNN1 | S. cerevisiae | 1,3-mannosyltransferase | Golgi (trans) |
| OCH1 | P. pastoris | 1,6-mannosyltransferase | Golgi (cis) |
| 2,6 ST | H. sapiens | 2,6-sialyltransferase | trans Golgi network |
| UDP-Gal T | S. pombe | UDP-Gal transporter | Golgi |
| Mnt1 | S. cerevisiae | 1,2-mannosyltransferase | Golgi (cis) |
| HDEL at C-terminus (SEQ ID NO: 5) | S. cerevisiae | retrieval signal | ER |

In any case, it is highly preferred that signal sequences are selected which are appropriate for the enzymatic activity or activities which are to be engineered into the host. For example, in developing a modified microorganism capable of terminal sialylation of nascent N-glycans, a process which occurs in the late Golgi in humans, it is desirable to utilize a sub-library of signal sequences derived from late Golgi proteins. Similarly, the trimming of $Man_8GlcNAc_2$ by an α-1,2-mannosidase to give $Man_5GlcNAc_2$ is an early step in complex N-glycan formation in humans. It is therefore desirable to have this reaction occur in the ER or early Golgi of an engineered host microorganism. A sub-library encoding ER and early Golgi retention signals is used.

In a preferred embodiment, a DNA library is then constructed by the in-frame ligation of a sub-library including DNA encoding signal sequences with a sub-library including DNA encoding glycosylation enzymes or catalytically active fragments thereof. The resulting library includes synthetic genes encoding fusion proteins. In some cases it is desirable to provide a signal sequence at the N-terminus of a fusion protein, or in other cases at the C-terminus. In some cases signal sequences may be inserted within the open reading frame of an enzyme, provided the protein structure of individual folded domains is not disrupted.

The method is most effective when a DNA library transformed into the host contains a large diversity of sequences, thereby increasing the probability that at least one transformant will exhibit the desired phenotype. Accordingly, prior to transformation, a DNA library or a constituent sub-library may be subjected to one or more rounds of gene shuffling, error prone PCR, or in vitro mutagenesis.

Transformation

The DNA library is then transformed into the host organism. In yeast, any convenient method of DNA transfer may be used, such as electroporation, the lithium chloride method, or the spheroplast method. To produce a stable strain suitable for high-density fermentation, it is desirable to integrate the DNA library constructs into the host chromosome. In a preferred embodiment, integration occurs via homologous recombination, using techniques known in the art. For example, DNA library elements are provided with flanking sequences homologous to sequences of the host organism. In this manner integration occurs at a defined site in the host genome, without disruption of desirable or essential genes. In an especially preferred embodiment, library DNA is integrated into the site of an undesired gene in a host chromosome, effecting the disruption or deletion of the gene. For example, integration into the sites of the OCH1, MNN1, or MNN4 genes allows the expression of the desired library DNA while preventing the expression of enzymes involved in yeast hypermannosylation of glycoproteins. In other embodiments, library DNA may be introduced into the host via a chromosome, plasmid, retroviral vector, or random integration into the host genome. In any case, it is generally desirable to include with each library DNA construct at least one selectable marker gene to allow ready selection of host organisms that have been stably transformed. Recyclable marker genes such as ura3, which can be selected for or against, are especially suitable.

Selection Process

After transformation of the host strain with the DNA library, transformants displaying the desired glycosylation phenotype are selected. Selection may be performed in a single step or by a series of phenotypic enrichment and/or depletion steps using any of a variety of assays or detection methods. Phenotypic characterization may be carried out manually or using automated high-throughput screening equipment. Commonly a host microorganism displays protein N-glycans on the cell surface, where various glycoproteins are localized. Accordingly intact cells may be screened for a desired glycosylation phenotype by exposing the cells to a lectin or antibody that binds specifically to the desired N-glycan. A wide variety of oligosaccharide-specific lectins are available commercially (EY Laboratories, San Mateo, Calif.). Alternatively, antibodies to specific human or animal N-glycans are available commercially or may be produced using standard techniques. An appropriate lectin or antibody may be conjugated to a reporter molecule, such as a chromophore, fluorophore, radioisotope, or an enzyme having a chromogenic substrate (Guillen et al., 1998. *Proc. Natl. Acad. Sci. USA* 95(14): 7888-7892). Screening may then be performed using analytical methods such as spectrophotometry, fluorimetry, fluorescence activated cell sorting, or scintillation counting. In other cases, it may be necessary to analyze isolated glycoproteins or N-glycans from transformed cells. Protein isolation may be carried out by techniques known in the art. In cases where an isolated N-glycan is required, an enzyme such as endo-β-N-acetylglucosaminidase (Genzyme Co., Boston, Mass.) may be used to cleave the N-glycans from glycoproteins. Isolated proteins or N-glycans may then be analyzed by liquid chromatography (e.g. HPLC), mass spectroscopy, or other suitable means. U.S. Pat. No. 5,595, 900 teaches several methods by which cells with desired extracellular carbohydrate structures may be identified. Prior to selection of a desired transformant, it may be desirable to deplete the transformed population of cells having undesired phenotypes. For example, when the method is used to engineer a functional mannosidase activity into cells, the desired transformants will have lower levels of mannose in cellular glycoprotein. Exposing the transformed population to a lethal radioisotope of mannose in the medium depletes the population of transformants having the undesired phenotype, i.e. high levels of incorporated mannose. Alternatively, a cytotoxic lectin or antibody, directed against an undesirable N-glycan, may be used to deplete a transformed population of undesired phenotypes.

Methods for Providing Sugar Nucleotide Precursors to the Golgi Apparatus

For a glycosyltransferase to function satisfactorily in the Golgi, it is necessary for the enzyme to be provided with a sufficient concentration of an appropriate nucleotide sugar, which is the high-energy donor of the sugar moiety added to a nascent glycoprotein. These nucleotide sugars to the appropriate compartments are provided by expressing an exogenous gene encoding a sugar nucleotide transporter in the host microorganism. The choice of transporter enzyme is influenced by the nature of the exogenous glycosyltransferase being used. For example, a GlcNAc transferase may require a UDP-GlcNAc transporter, a fucosyltransferase may require a GDP-fucose transporter, a galactosyltransferase may require a UDP-galactose transporter, or a sialyltransferase may require a CMP-sialic acid transporter.

The added transporter protein conveys a nucleotide sugar from the cytosol into the Golgi apparatus, where the nucleotide sugar may be reacted by the glycosyltransferase, e.g. to elongate an N-glycan. The reaction liberates a nucleoside diphosphate or monophosphate, e.g. UDP, GDP, or CMP. As accumulation of a nucleoside diphosphate inhibits the further activity of a glycosyltransferase, it is frequently also desirable to provide an expressed copy of a gene encoding a nucleotide diphosphatase. The diphosphatase (specific for UDP or GDP as appropriate) hydrolyzes the diphosphonucleoside to yield a nucleoside monophosphate and inorganic phosphate. The nucleoside monophosphate does not inhibit the glycotransferase and in any case is exported from the Golgi by an endogenous cellular system. Suitable transporter enzymes, which are typically of mammalian origin, are described below.

EXAMPLES

The use of the above general method may be understood by reference to the following non-limiting examples. Examples of preferred embodiments are also summarized in Table 6.

Example 1

Engineering of *P. pastoris* with α-1,2-Mannosidase to Produce Interferon

An α-1,2-mannosidase is required for the trimming of $Man_8GlcNAc_2$ to yield $Man_5GlcNAc_2$, an essential intermediate for complex N-glycan formation. An OCH1 mutant of *P. pastoris* is engineered to express secreted human interferon-β under the control of an aox promoter. A DNA library is constructed by the in-frame ligation of the catalytic domain of human mannosidase IB (an α-1,2-mannosidase) with a sub-library including sequences encoding early Golgi localization peptides. The DNA library is then transformed into the host organism, resulting in a genetically mixed population wherein individual transformants each express interferon-β as well as a synthetic mannosidase gene from the library. Individual transformant colonies are cultured and the production of interferon is induced by addition of methanol. Under these conditions, over 90% of the secreted protein includes interferon-β. Supernatants are purified to remove salts and low-molecular weight contaminants by $C_{18}$ silica reversed-phase chromatography. Desired transformants expressing appropriately targeted, active α-1,2-mannosidase produce interferon-β including N-glycans of the structure $Man_5GlcNAc_2$, which has a reduced molecular mass compared to the interferon of the parent strain. The purified supernatants including interferon-β are analyzed by MALDI-TOF mass spectroscopy and colonies expressing the desired form of interferon-β are identified.

Example 2

Engineering of Strain to Express GlcNAc Transferase I

GlcNAc Transferase I activity is required for the maturation of complex N-glycans. $Man_5GlcNAc_2$ may only be trimmed by mannosidase II, a necessary step in the formation of human glycoforms, after the addition of GlcNAc to the terminal α-1,3 mannose residue by GlcNAc Transferase I (Schachter, 1991 Glycobiology 1(5):453-461). Accordingly a library is prepared including DNA fragments encoding suitably targeted GlcNAc Transferase I genes. The host organism is a strain, e.g. a yeast, that is deficient in hypermannosylation (e.g. an OCH1 mutant), provides the substrate UDP-GlcNAc in the Golgi and/or ER, and provides N-glycans of the structure $Man_5GlcNAc_2$ in the Golgi and/or ER. After transformation of the host with the DNA library, the transformants are screened for those having the highest concentration of terminal GlcNAc on the cell surface, or alternatively secrete the protein having the highest terminal GlcNAc content. Such a screen is performed using a visual method (e.g. a staining procedure), a specific terminal GlcNAc binding antibody, or a lectin. Alternatively the desired transformants exhibit reduced binding of certain lectins specific for terminal mannose residues.

Example 3

Engineering of Strains with a Mannosidase II

In another example, it is desirable in order to generate a human glycoform in a microorganism to remove the two remaining terminal mannoses from the structure $GlcNAcMan_5GlcNAc_2$ by action of a mannosidase II. A DNA library including sequences encoding cis and medial Golgi localization signals is fused in-frame to a library encoding mannosidase II catalytic domains. The host organism is a strain, e.g. a yeast, that is deficient in hypermannosylation (e.g. an OCH1 mutant) and provides N-glycans having the structure $GlcNAcMan_5GlcNAc_2$ in the Golgi and/or ER. After transformation, organisms having the desired glycosylation phenotype are selected. An in vitro assay is used in one method. The desired structure $GlcNAcMan_3GlcNAc_2$ (but not the undesired $GlcNAcMan_5GlcNAc_2$) is a substrate for the enzyme GlcNAc Transferase II. Accordingly, single colonies may be assayed using this enzyme in vitro in the presence of the substrate, UDP-GlcNAc. The release of UDP is determined either by HPLC or an enzymatic assay for UDP. Alternatively radioactively labeled UDP-GlcNAc is used.

The foregoing in vitro assays are conveniently performed on individual colonies using high-throughput screening equipment. Alternatively a lectin binding assay is used. In this case the reduced binding of lectins specific for terminal mannoses allows the selection of transformants having the desired phenotype. For example, *Galantus nivalis* lectin binds specifically to terminal α-1,3-mannose, the concentration of which is reduced in the presence of operatively expressed mannosidase II activity. In one suitable method, *G. nivalis* lectin attached to a solid agarose support (available from Sigma Chemical, St. Louis, Mo.) is used to deplete the transformed population of cells having high levels of terminal α-1,3-mannose.

Example 4

Engineering of Organisms to Express Sialyltransferase

The enzymes α2,3-sialyltransferase and α2,6-sialyltransferase add terminal sialic acid to galactose residues in nascent human N-glycans, leading to mature glycoproteins. In human the reactions occur in the trans Golgi or TGN. Accordingly a DNA library is constructed by the in-frame fusion of sequences encoding sialyltransferase catalytic domains with sequences encoding trans Golgi or TGN localization signals. The host organism is a strain, e.g. a yeast, that is deficient in hypermannosylation (e.g. an OCH1 mutant), which provides N-glycans having terminal galactose residues in the trans Golgi or TGN, and provides a sufficient concentration of CMP-sialic acid in the trans Golgi or TGN. Following transformation, transformants having the desired phenotype are selected using a fluorescent antibody specific for N-glycans having a terminal sialic acid.

Example 5

Method of Engineering Strains to Express UDP-GlcNAc Transporter

The cDNA of human Golgi UDP-GlcNAc transporter has been cloned by Ishida and coworkers. (Ishida, N., et al. 1999 *J. Biochem.* 126(1): 68-77. Guillen and coworkers have cloned the canine kidney Golgi UDP-GlcNAc transporter by phenotypic correction of a *Kluyveromyces lactis* mutant deficient in Golgi UDP-GlcNAc transport. (Guillen, E., et al. 1998). Thus a mammalian Golgi UDP-GlcNAc transporter gene has all of the necessary information for the protein to be expressed and targeted functionally to the Golgi apparatus of yeast.

Example 6

Method of Engineering Strains to Express GDP-Fucose Transporter

The rat liver Golgi membrane GDP-fucose transporter has been identified and purified by Puglielli, L. and C. B. Hirschberg 1999 *J. Biol. Chem.* 274(50):35596-35600. The corresponding gene can be identified using standard techniques, such as N-terminal sequencing and Southern blotting using a degenerate DNA probe. The intact gene can is then be expressed in a host microorganism that also expresses a fucosyltransferase.

Example 7

Method of engineering Strains to Express UDP-Galactose Transporter

Human UDP-galactose (UDP-Gal) transporter has been cloned and shown to be active in *S. cerevisiae*. (Kainuma, M., et al. 1999 *Glycobiology* 9(2): 133-141). A second human UDP-galactose transporter (hUGT1) has been cloned and functionally expressed in Chinese Hamster Ovary Cells. Aoki, K., et al. 1999 *J. Biochem.* 126(5): 940-950. Likewise Segawa and coworkers have cloned a UDP-galactose transporter from *Schizosaccharomyces pombe* (Segawa, H., et al. 1999 *Febs Letters* 451(3): 295-298).

CMP-Sialic Acid Transporter

Human CMP-sialic acid transporter (hCST) has been cloned and expressed in Lec 8 CHO cells by Aoki and coworkers (1999). Molecular cloning of the hamster CMP-sialic acid transporter has also been achieved (Eckhardt and Gerardy Schahn 1997 *Eur. J. Biochem.* 248(1): 187-192). The functional expression of the murine CMP-sialic acid transporter was achieved in *Saccharomyces cerevisiae* by Beminsone, P., et al. 1997 *J. Biol. Chem.* 272(19):12616-12619.

TABLE 6

Examples of preferred embodiments of the methods for modifying glycosylation in a eukaroytic microorganism, e.g. *Pichia pastoris*

| Desired Structure | Suitable Catalytic Activities | Suitable Sources of Localization Sequences | Suitable Gene Deletions | Suitable Transporters and/or Phosphatases |
|---|---|---|---|---|
| Man$_5$GlcNAc$_2$ | α-1,2-mannosidase (murine, human, *Bacillus* sp., *A. nidulans*) | Mns1 (N-terminus, *S. cerevisiae*) Och1 (N-terminus, *S. cerevisiae*, *P. pastoris*) Ktr1 Mnn9 Mnt1 (*S. cerevisiae*) KDEL (SEQ ID NO: 6), HDEL (SEQ ID NO: 5) (C-terminus) | OCH1 MNN4 MNN6 | none |
| GlcNAcMan$_5$GlcNAc$_2$ | GlcNAc Transferase I, (human murine, rat etc.) | Och1 (N-terminus, *S. cerevisiae*, *P. pastoris*) KDEL (SEQ ID NO: 6), HDEL (SEQ ID NO: 5) (C-terminus) Mnn1 (N-terminus, *S. cerevisiae*) Mnt1 (N-terminus, *S. cerevisiae*) GDPase (N-terminus, *S. cerevisiae*) | OCH1 MNN4 MNN6 | UDP-GlcNAc transporter (human, murine, *K. lactis*) UDPase (human) |

TABLE 6-continued

Examples of preferred embodiments of the methods for modifying glycosylation in a eukaroytic microorganism, e.g. Pichia pastoris

| Desired Structure | Suitable Catalytic Activities | Suitable Sources of Localization Sequences | Suitable Gene Deletions | Suitable Transporters and/or Phosphatases |
|---|---|---|---|---|
| GlcNAcMan$_3$GlcNAc$_2$ | mannosidase II | Ktr1<br>Mnn1 (N-terminus, S. cerevisiae)<br>Mnt1(N-terminus, S. cerevisiae)<br>Kre2/Mnt1 (S. cerevisiae)<br>Kre2 (P. pastoris)<br>Ktr1 (S. cerevisiae)<br>Ktr1 (P. pastoris)<br>Mnn1 (S. cerevisiae) | OCH1<br>MNN4<br>MNN6 | UDP-GlcNAc transporter (human, murine, K. lactis)<br>UDPase (human) |
| GlcNAc$_{(2-4)}$Man$_3$GlcNAc$_2$ | GlcNAc Transferase II, III, IV, V (human, murine) | Mnn1 (N-terminus, S. cerevisiae)<br>Mnt1 (N-terminus, S. cerevisiae)<br>Kre2/Mnt1 (S. cerevisiae)<br>Kre2 (P. pastoris)<br>Ktr1 (S. cerevisiae)<br>Ktr1 (P. pastoris)<br>Mnn1 (S. cerevisiae) | OCH1<br>MNN4<br>MNN6 | UDP-GlcNAc transporter (human, murine, K. lactis)<br>UDPase (human) |
| Gal$_{(1-4)}$GlcNAc$_{(2-4)}$-Man$_3$GlcNAc$_2$ | β-1,4-Galactosyl transferase (human) | Mnn1 (N-terminus, S. cerevisiae)<br>Mnt1(N-terminus, S. cerevisiae)<br>Kre2/Mnt1 (S. cerevisiae)<br>Kre2 (P. pastoris)<br>Ktr1 (S. cerevisiae)<br>Ktr1 (P. pastoris)<br>Mnn1 (S. cerevisiae) | OCH1<br>MNN4<br>MNN6 | UDP-Galactose transporter (human, S. pombe) |
| NANA$_{(1-4)}$-Gal$_{(1-4)}$GlcNAc$_{(2-4)}$-Man$_3$GlcNAc$_2$ | α-2,6-Sialyltransferase (human)<br>α-2,3-Sialyltransferase | KTR1<br>MNN1 (N-terminus, S. cerevisiae)<br>MNT1 (N-terminus, S. cerevisiae)<br>Kre2/Mnt1 (S. cerevisiae)<br>Kre2 (P. pastoris)<br>Ktr1 (S. cerevisiae)<br>Ktr1 (P. pastoris)<br>MNN1 (S. cerevisiae) | OCH1<br>MNN4<br>MNN6 | CMP-Sialic acid transporter (human) |

TABLE 7

DNA and Protein Sequence Resources

1. European Bioinformatics Institute (EBI) is a centre for research and services in bioinformatics
2. Swissprot database
3. List of known glycosyltransferases and their origin.
   β1,2 (GnT I) EC 2.4.1.101

4. human cDNA, Kumar et al (1990) Proc. Natl. Acad. Sci. USA 87: 9948-9952
5. human gene, Hull et al (1991) Biochem. Biophys. Res. Commun. 176: 608-615
6. mouse cDNA, Kumar et al (1992) Glycobiology 2: 383-393
7. mouse gene, Pownall et al (1992) Genomics 12: 699-704
8. murine gene (5' flanking, non-coding), Yang et al (1994) Glycobiology 5: 703-712
9. rabbit cDNA, Sarkar et al (1991) Proc. Natl. Acad. Sci. USA 88: 234-238
10. rat cDNA, Fukada et al (1994) Biosci.Biotechnol.Biochem. 58: 200-201
    1,2 (GnT II) EC 2.4.1.143

11. human gene, Tan et al (1995) Eur. J. Biochem. 231: 317-328
12. rat cDNA, D'Agostaro et al (1995) J. Biol. Chem. 270: 15211-15221
13. β1,4 (GnT III) EC 2.4.1.144
14. human cDNA, Ihara et al (1993) J. Biochem.113: 692-698
15. murine gene, Bhaumik et al (1995) Gene 164: 295-300
16. rat cDNA, Nishikawa et al (1992) J. Biol. Chem. 267: 18199-18204
    β1,4 (GnT IV) EC 2.4.1.145

17. human cDNA, Yoshida et al (1998) Glycoconjugate Journal 15: 1115-1123
18. bovine cDNA, Minowa et al., European Patent EP 0 905 232
    β1,6 (GnT V) EC 2.4.1.155

TABLE 7-continued

DNA and Protein Sequence Resources 19. human cDNA, Saito et al (1994) Biochem. Biophys. Res. Commun. 198: 318-327
20. rat cDNA, Shoreibah et al (1993) J. Biol. Chem. 268: 15381-15385

β1,4 Galactosyltransferase, EC 2.4.1.90 (LacNAc synthetase)
EC 2.4.1.22 (lactose synthetase)

21. bovine cDNA, D'Agostaro et al (1989) Eur. J. Biochem. 183: 211-217
22. bovine cDNA (partial), Narimatsu et al (1986) Proc. Natl. Acad. Sci. USA 83: 4720-4724
23. bovine cDNA (partial), Masibay & Qasba (1989) Proc. Natl. Acad. Sci. USA 86: 5733-5377
24. bovine cDNA (5' end), Russo et al (1990) J. Biol. Chem. 265: 3324
25. chicken cDNA (partial), Ghosh et al (1992) Biochem. Biophys. Res. Commun. 1215-1222
26. human cDNA, Masri et al (1988) Biochem. Biophys. Res. Commun. 157: 657-663
27. human cDNA, (HeLa cells) Watzele & Berger (1990) Nucl. Acids Res. 18: 7174
28. human cDNA, (partial) Uejima et al (1992) Cancer Res. 52: 6158-6163
29. human cDNA, (carcinoma) Appert et al (1986) Biochem. Biophys. Res. Commun. 139: 163-168
30. human gene, Mengle-Gaw et al (1991) Biochem. Biophys. Res. Commun. 176: 1269-1276
31. murine cDNA, Nakazawa et al (1988) J. Biochem. 104: 165-168
32. murine cDNA, Shaper et al (1988) J. Biol. Chem. 263: 10420-10428
33. murine cDNA (novel), Uehara & Muramatsu unpublished
34. murine gene, Hollis et al (1989) Biochem. Biophys. Res. Commun. 162: 1069-1075
35. rat protein (partial), Bendiak et al (1993) Eur. J. Biochem. 216: 405-417

2,3-Sialyltransferase, (ST3Gal II) (N-linked) (Gal-1,3/4-GlcNAc) EC 2.4.99.6

36. human cDNA, Kitagawa & Paulson (1993) Biochem. Biophys. Res. Commun. 194: 375-382
37. rat cDNA, Wen et al (1992) J. Biol. Chem. 267: 21011-21019

2,6-Sialyltransferase, (ST6Gal I) EC 2.4.99.1

38. chicken, Kurosawa et al (1994) Eur. J. Biochem 219: 375-381
39. human cDNA (partial), Lance et al (1989) Biochem. Biophys. Res. Commun. 164: 225-232
40. human cDNA, Grundmann et al (1990) Nucl. Acids Res. 18: 667
41. human cDNA, Zettlmeisl et al (1992) Patent EPO475354-A/3
42. human cDNA, Stamenkovic et al (1990) J. Exp. Med. 172: 641-643 (CD75)
43. human cDNA, Bast et al (1992) J. Cell Biol. 116: 423-435
44. human gene (partial), Wang et al (1993) J. Biol. Chem. 268: 4355-4361
45. human gene (5' flank), Aasheim et al (1993) Eur. J. Biochem. 213: 467-475
46. human gene (promoter), Aas-Eng et al (1995) Biochim. Biophys. Acta 1261: 166-169
47. mouse cDNA, Hamamoto et al (1993) Bioorg. Med. Chem. 1: 141-145
48. rat cDNA, Weinstein et al (1987) J. Biol. Chem. 262: 17735-17743
49. rat cDNA (transcript fragments), Wang et al (1991) Glycobiology 1: 25-31, Wang et al (1990) J. Biol. Chem. 265: 17849-17853
50. rat cDNA (5' end), O'Hanlon et al (1989) J. Biol. Chem. 264: 17389-17394; Wang et al (1991) Glycobiology 1: 25-31
51. rat gene (promoter), Svensson et al (1990) J. Biol. Chem. 265: 20863-20688
52. rat mRNA (fragments), Wen et al (1992) J. Biol. Chem. 267: 2512-2518

Additional methods and reagents which can be used in the methods for modifying the glycosylation are described in the literature, such as U.S. Pat. Nos. 5,955,422, 4,775,622, 6,017,743, 4,925,796, 5,766,910, 5,834,251, 5,910,570, 5,849,904, 5,955,347, 5,962,294, 5,135,854, 4,935,349, 5,707,828, and 5,047,335.

Appropriate yeast expression systems can be obtained from sources such as the American Type Culture Collection, Rockville, Md. Vectors are commercially available from a variety of sources.

I claim:

1. A yeast or filamentous fungal host cell comprising a nucleic acid encoding a GlcNAc transferase I enzyme selected to have optimal activity in the ER or Golgi of said host cell, the enzyme comprising:
   (a) a GlcNAc transferase I catalytic domain having optimal activity in said endoplasmatic reticulum (ER) or Golgi at a pH between 5.1 and 8.0; fused to
   (b) a cellular targeting signal peptide not normally associated with the catalytic domain selected to target the GlcNAc transferase I catalytic domain to the ER or Golgi apparatus of the host cell,
   wherein said host cell is capable of producing recombinant glycoproteins wherein an excess of 30 mole % of the N-glycan structures attached thereto have a Man$_5$GlcNAc$_2$, structure that can serve as a substrate for GlcNAc transferase I in vivo.

2. The host cell of claim 1, wherein the host cell further comprises a nucleotide sugar transporter or a nucleotide diphosphatase.

3. The host cell of claim 1 selected from the group consisting of *Pichia* sp., *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, and *Pichia methanolica, Saccharomyces* sp., *Saccharomyces cerevisiae, Hansenula polymorpha, Kluyveromyces* sp., *Candida albicans, Aspergillus nidulans*, and *Trichoderma reesei*.

4. The host cell of claim 1, wherein the host cell further comprises a nucleic acid encoding one or more additional polypeptides selected from the group consisting of glycosidases, glycosyltransferases, nucleotide sugar transporters, or nucleotide diphosphatases.

5. The host cell of claim 4, wherein the glycosyltransferase is selected from the group consisting of N-acetylglucosamine transferase (GnT) GnT II, GnT III, GnT IV, GnT V, GnT VI, galactosyl transferase (galT), fucosyltransferase, and sialyltransferase (ST).

6. The host cell of claim 4, wherein the nucleotide transporter is selected from the group consisting of UDP-GlcNAc transporter, UDP-galactose transporter, GDP-fucose transporter and CMP-sialic acid transporter.

7. The host cell of claim 4, wherein at least one of said one or more additional polypeptides is a fusion protein between a catalytic domain of an enzyme selected from the group consisting of glycosidases, glycosyltransferases, nucleotide sugar transporters, or nucleotide diphosphatases and a cellular targeting signal peptide.

8. The host cell of claim 7, wherein said fusion protein is encoded by at least one genetic construct formed by the in-frame ligation of a nucleic acid encoding a cellular targeting signal peptide with a nucleic acid encoding a catalytic domain of the enzyme.

9. The host cell of claim 4, wherein the host cell expresses a UDP-GlcNAc transporter.

10. The host cell of claim 4, wherein the host cell expresses a UDP-or GDP specific diphosphatase.

11. The host cell of claim 1, wherein at least one nucleic acid molecule encoding a glycosylation enzyme is introduced into the host cell by integration into the host cell chromosome.

12. The host cell of claim 4, wherein at least one of said one or more additional polypeptides is a mannosidase II.

13. The host cell of claim 4, wherein the host cell is capable of producing glycoproteins comprising one or more sugars selected from the group consisting of N-acetylglucosamine, galactose, sialic acid, and fucose.

14. The host cell of claim 4, wherein the host cell is capable of producing glycoproteins comprising at least one oligosaccharide branch comprising the structure NeuNAc-Gal-GlcNAc-Man.

15. The host cell of claim 1, wherein the host cell lacks the activity of one or more enzymes selected from the group consisting of mannosyltransferases and phosphomannosyltransferases.

16. The host cell of claim 15, wherein the host cell lacks an enzyme activity with respect to the N-glycan on a glycoprotein, the deficient activity selected from the group consisting of 1,6 mannosyltransferase, 1,3 mannosyltransferase, and 1,2 mannosyltransferase.

17. The host cell of claim 1, wherein the host is an OCH1 mutant of $P.$ $pastoris$.

18. The host cell of claim 1, wherein the host cell is genetically modified to further express
   (a) a mannosidase II catalytic domain fused to
   (b) a cellular targeting signal peptide not normally associated with the catalytic domain selected to target the mannosidase II catalytic domain to the ER or Golgi apparatus of the host cell.

19. The host cell of claim 18, wherein the host cell is genetically modified to further express
   (a) a GlcNAc transferase II catalytic domain fused to
   (b) a cellular targeting signal peptide not normally associated with the catalytic domain selected to target the GlcNAc transferase II catalytic domain to the ER or Golgi apparatus of the host cell.

20. The host cell of claim 19, wherein the host cell is genetically modified to further express
   (a) a galactosyltransferase catalytic domain fused to
   (b) a cellular targeting signal peptide not normally associated with the catalytic domain selected to target the galactosyltransferase catalytic domain to the ER or Golgi apparatus of the host cell.

21. The host cell of claim 20, wherein the host cell is genetically modified to further express
   (a) a sialyltransferase catalytic domain fused to
   (b) a cellular targeting signal peptide not normally associated with the catalytic domain selected to target the sialyltransferase catalytic domain to the ER or Golgi apparatus of the host cell.

* * * * *